United States Patent
Anderberg et al.

(10) Patent No.: US 9,733,261 B2
(45) Date of Patent: Aug. 15, 2017

(54) METHODS AND COMPOSITIONS FOR DIAGNOSIS AND PROGNOSIS OF STROKE OR OTHER CEREBRAL INJURY

(71) Applicant: ASTUTE MEDICAL, INC., San Diego, CA (US)

(72) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US); James Patrick Kampf, San Diego, CA (US)

(73) Assignee: Astute Medical, Inc., San Diego, CA (US)

( * ) Notice: Subject to any disclaimer, the term of this patent is extended or adjusted under 35 U.S.C. 154(b) by 0 days.

(21) Appl. No.: 14/396,377

(22) PCT Filed: Apr. 24, 2013

(86) PCT No.: PCT/US2013/038067
§ 371 (c)(1),
(2) Date: Oct. 22, 2014

(87) PCT Pub. No.: WO2013/163345
PCT Pub. Date: Oct. 31, 2013

(65) Prior Publication Data
US 2015/0119269 A1 Apr. 30, 2015

Related U.S. Application Data

(60) Provisional application No. 61/637,813, filed on Apr. 24, 2012, provisional application No. 61/637,815, filed on Apr. 24, 2012, provisional application No. 61/674,650, filed on Jul. 23, 2012, provisional application No. 61/674,656, filed on Jul. 23, 2012, provisional application No. 61/674,660, filed on Jul. 23, 2012.

(51) Int. Cl.
*G01N 33/68* (2006.01)
*G01N 33/573* (2006.01)
*G01N 33/74* (2006.01)

(52) U.S. Cl.
CPC ....... *G01N 33/6896* (2013.01); *G01N 33/573* (2013.01); *G01N 33/6863* (2013.01); *G01N 33/6869* (2013.01); *G01N 33/74* (2013.01); *G01N 33/746* (2013.01); *G01N 2800/2871* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,480,792 A | 1/1996 | Buechler |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs |
| 5,885,527 A | 3/1999 | Buechler |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler |
| 6,057,098 A | 5/2000 | Buechler et al. |
| 6,113,855 A | 9/2000 | Buechler et al. |
| 6,143,576 A | 11/2000 | Buechler |
| 2005/0255484 A1 | 11/2005 | Valkirs et al. |
| 2008/0220013 A1* | 9/2008 | Hochstrasser ..... G01N 33/6893 424/198.1 |
| 2009/0239241 A1 | 9/2009 | Ray et al. |

FOREIGN PATENT DOCUMENTS

| | | |
|---|---|---|
| EP | 2166358 A1 | 3/2010 |
| WO | 2011075744 A1 | 6/2011 |

OTHER PUBLICATIONS

Lalkhen and McCluskey, Continuing Education in Anaesthesia, Critical Care & Pain, 2008; 8: 221-223.*
The International Search Report and Written Opinion issued in PCT/US2013/038067 on Sep. 18, 2013 (17 pages).
Devran et al., "C-reactive protein as a predictor of mortality in patients affected with severe sepsis in intensive care unit", Multidisciplinary Respiratory Medicine 2012, 7:47; http://www.mrmjournal.com/content/7/1/47 (6 pages).
Indik and Alpert, "Detection of Pulmonary Embolism by D-Dimer Assay, Spiral Computed Tomography, and Magnetic Resonance Imaging", Progress in Cardiovascular Diseases, vol. 42, No. 4 (Jan./Feb.), 2000: pp. 261-272.
Sykes et al., "Analytical Relationships Among Biosite, Bayer, and Roche Methods for BNP and NT-proBNP", Am J Clin Pathol 2005;123:584-590; DOI: 10.1309/F86FVEFDGX06DTUV.
"C-reactive protein", at URL http://www.nlm.nih.gov/medlineplus/ency/article/003356.htm, C-reactive protein: MedlinePlus Medical Encyclopedia, retrieved Jul. 31, 2015 (4 pages).
Extended European Search Report and Written Opinion issued in EP 13782208 dated Mar. 30, 2016.
Cwirla et al., Peptides on phage: a vast library of peptides for identifying ligands. Proc Natl Acad Sci USA. Aug. 1990;87(16):6378-6382.

(Continued)

*Primary Examiner* — Christina Borgeest
(74) *Attorney, Agent, or Firm* — Acuity Law Group, PC; Michael Whittaker

(57) ABSTRACT

The present invention relates to methods and compositions for monitoring, diagnosis, prognosis, and determination of treatment regimens in stroke patients and in patients at risk for stroke. In particular, the invention relates to using assays that detect one or more biomarkers as diagnostic and prognostic biomarker assays in such patients.

6 Claims, No Drawings

(56) References Cited

OTHER PUBLICATIONS

Devlin et al., Random peptide libraries: a source of specific protein binding molecules Science. Jul. 27, 1990;249(4967):404-406.

Fischer et al., A readers' guide to the interpretation of diagnostic test properties: clinical example of sepsis. Intensive Care Med. Jul. 2003;29(7):1043-1051.

Nelson and Griswold, A computer program for calculating antibody affinity constants. Comput Methods Programs Biomed. Jul.-Aug., 1988;27(1):65-68.

Reynolds et al., Early Biomarkers of Stroke. Clin Chem. Oct. 2003;49(10):1733-1739.

Scott and Smith, Searching for peptide ligands with an epitope library. Science. Jul. 27, 1990;249(4967):386-390.

van Erp et al., Application of a sol particle immunoassay to the determination of affinity constants of monoclonal antibodies. J Immunoassay. 1991;12(3):425-443.

Ward et al., Binding activities of a repertoire of single immunoglobulin variable domains secreted from *Escherichia coli*. Nature. Oct. 12, 1989;341(6242):544-546.

Wilson et al., Simplified conjugation chemistry for coupling peptides to F(ab') fragments: autologous red cell agglutination assay for HIV-1 antibodies. J Immunol Methods. Oct. 14, 1994;175(2):267-273.

Yarmush et al., Coupling of antibody-binding fragments to solid-phase supports: site-directed binding of F(ab')2 fragments. J Biochem Biophys Methods. Dec. 1992;25(4):285-297.

* cited by examiner

US 9,733,261 B2

METHODS AND COMPOSITIONS FOR DIAGNOSIS AND PROGNOSIS OF STROKE OR OTHER CEREBRAL INJURY

The present invention is filed under 35 U.S.C. §371 as the U.S. national phase of International Application No. PCT/US2013/038067, filed Apr. 24, 2013, which designated the U.S. and claims priority to U.S. Provisional Patent Applications 61/637,813 filed Apr. 24, 2012; 61/637,815 filed Apr. 24, 2012; 61/674,650 filed Jul. 23, 2012; 61/674,656 filed Jul. 23, 2012; and 61/674,660 filed Jul. 23, 2012, each of which is hereby incorporated by reference in its entirety.

BACKGROUND OF THE INVENTION

The following discussion of the background of the invention is merely provided to aid the reader in understanding the invention and is not admitted to describe or constitute prior art to the present invention.

Stroke is a manifestation of vascular injury to the brain which is commonly secondary to atherosclerosis or hypertension, and is the third leading cause of death (and the second most common cause of neurologic disability) in the United States. Stroke can be categorized into two broad types, "ischemic stroke" and "hemorrhagic stroke." Additionally, a patient may experience transient ischemic attacks, which share the same underlying cause as strokes and which cause the same symptoms. The similarity of these acute clinical syndromes made it difficult to differentiate them; they were distinguished on the basis of an arbitrary criterion for the duration of symptoms. While the damage from a TIA may be just as severe as a stroke, the symptoms of a TIA can resolve within a few minutes or 24 hours. For purposes of the present invention, ischemic stroke and hemorrhagic stroke and TIA will all be referred to as "strokes."

Ischemic brain injury encompasses thrombotic, embolic, lacunar and hypoperfusion types of strokes. Thrombi are occlusions of arteries created in situ within the brain, while emboli are occlusions caused by material from a distant source, such as the heart and major vessels, often dislodged due to myocardial infarct or atrial fibrillation. Less frequently, thrombi may also result from vascular inflammation due to disorders such as meningitis. Thrombi or emboli can result from atherosclerosis or other disorders, for example, arteritis, and lead to physical obstruction of arterial blood supply to the brain. Lacunar stroke refers to an infarct within non-cortical regions of the brain. Hypoperfusion embodies diffuse injury caused by non-localized cerebral ischemia, typically caused by myocardial infarction and arrhythmia.

The onset of ischemic brain injury is often abrupt, and can become an "evolving stroke" manifested by neurologic deficits that worsen over a 24-48 hour period. In evolving stroke, "stroke-associated symptom(s)" commonly include unilateral neurologic dysfunction that extends progressively, without producing headache or fever. Evolving stroke may also become a "completed stroke," in which symptoms develop rapidly and are maximal within a few minutes.

Hemorrhagic stroke is caused by intracerebral or subarachnoid hemorrhage, i.e., bleeding into brain tissue, following blood vessel rupture within the brain. Intracerebral and subarachnoid hemorrhages are subsets of a broader category of hemorrhage referred to as intracranial hemorrhage. Intracerebral hemorrhage is typically due to chronic hypertension, and a resulting rupture of an arteriosclerotic vessel. Stroke-associated symptom(s) of intracerebral hemorrhage are abrupt, with the onset of headache and steadily increasing neurological deficits. Nausea, vomiting, delirium, seizures and loss of consciousness are additional common stroke-associated symptoms.

In contrast, most subarachnoid hemorrhage is caused by head trauma or aneurysm rupture which is accompanied by high pressure blood release which also causes direct cellular trauma. Prior to rupture, aneurysms may be asymptomatic, or occasionally associated with tension or migraine headaches. However, headache typically becomes acute and severe upon rupture, and may be accompanied by varying degrees of neurological deficit, vomiting, dizziness, and altered pulse and respiratory rates.

Concepts of brain ischemia and the temporal correlation with clinical events have changed considerably on the basis of studies using computed tomography (CT), magnetic resonance imaging (MRI), positron-emission tomography, and other imaging techniques. At most institutions, CT of the brain is performed as part of the initial evaluation of a patient with suspected stroke. The main advantage of this imaging modality is its widespread availability and sensitivity for hemorrhage. However, it is insensitive to early ischemic changes during acute cerebral ischemia. Several technologies based on MRI have shown promise for the early diagnosis of stroke. However, as a practical issue, most hospitals lack the necessary specialized MRI services in the acute setting.

Another approach to the diagnosis of acute stroke has been the evaluation of biomarkers in body fluid samples such as blood. By way of example, acute stroke has been associated with serum elevations of numerous biomarkers related to inflammation, coagulation, and glial cell damage in a variety of research studies. To date, however, no biomarker test has been demonstrated to possess the requisite sensitivity and specificity to allow it to function as a useful clinical diagnostic.

There remains a need in the art for a rapid, objective, clinically accurate, available diagnostic tool for aiding in the diagnosis and care of stroke patients.

BRIEF SUMMARY OF THE INVENTION

The present invention relates to the identification and use of diagnostic markers for stroke and cerebral injury. The methods and compositions described herein can meet the need in the art for rapid, sensitive and specific diagnostic assay to be used in the diagnosis and differentiation of various forms of stroke. Moreover, the methods and compositions of the present invention can also be used to facilitate the treatment of stroke patients and the development of additional diagnostic and/or prognostic indicators.

In various aspects, the invention relates to materials and procedures for identifying markers that are associated with the diagnosis, prognosis, or differentiation of stroke and/or TIA in a patient; to using such markers in diagnosing and treating a patient and/or to monitor the course of a treatment regimen; to using such markers to identify subjects at risk for one or more adverse outcomes related to stroke and/or TIA; and for screening compounds and pharmaceutical compositions that might provide a benefit in treating or preventing such conditions.

In a first aspect, the invention discloses methods for determining a diagnosis or prognosis related to cerebral injury, or for differentiating between types of strokes and/or TIA. As described herein, measurement of one or more biomarkers selected from the group consisting of Agouti-related protein, Alpha-2 macroglobulin, Alpha-fetoprotein, Amphiregulin, Angiopoietin-1 receptor, Angiopoietin-related protein 3, Angiopoietin-related protein 4, Angiopoietin-related protein 6, Bone morphogenetic protein 7, Cadherin-3, Cancer Antigen 15-3, Cancer Antigen 19-9, Carcinoembryonic antigen-related cell adhesion molecule 5, C—C motif chemokine 1, C—C motif chemokine 13, C—C motif chemokine 15, C—C motif chemokine 17, C—C motif chemokine 19, C—C motif chemokine 26, C—C motif chemokine 8, Choriogonadotropin subunit beta, Clusterin, C—X—C motif chemokine 11, C—X—C motif chemokine 6, C—X—C motif chemokine 9, Cyclin-dependent kinase inhibitor 1, Endoglin, Epiregulin, Epithelial cell adhesion molecule, Erythropoietin, Fatty acid-binding protein, liver, Fibroblast growth factor 19, Fibroblast growth factor 21, Fibroblast growth factor 23, Follistatin, Follitropin subunit beta, Galectin-3, Glial cell line-derived neurotrophic factor, Heat shock protein beta-1, Heparin-binding EGF-like growth factor, Heparin-binding growth factor 1, Hepatitis A virus cellular receptor 1, Hepatocyte growth factor receptor, Insulin receptor substrate 1, Insulin-like growth factor-binding protein 1, Insulin-like growth factor-binding protein 2, Insulin-like growth factor-binding protein 4, Intercellular adhesion molecule 3, Interleukin-1 receptor type I, Interleukin-1 receptor type II, Interleukin-11, Interleukin-21, Interleukin-28A, Interleukin-29, Interleukin-33, Interleukin-4 receptor alpha chain, Interleukin-6 receptor subunit alpha, Interleukin-6 receptor subunit beta, Keratin, type I cytoskeletal 19 (aa311-367), Kit ligand, Lutropin subunit beta, Lymphotactin, Macrophage colony-stimulating factor 1, Matrilysin, Metalloproteinase inhibitor 4, Growth-regulated alpha, beta, and gamma proteins (total), Mucin-16, Neprilysin, Neuronal cell adhesion molecule, NF-kappa-B inhibitor alpha, Osteocalcin, Oxidized low-density lipoprotein receptor 1, Parathyroid hormone, Platelet endothelial cell adhesion molecule, Probetacellulin, Pro-interleukin-16, Prolactin, Proprotein convertase subtilisin/kexin type 9, Prostate-specific antigen, Protein NOV homolog, Protransforming growth factor alpha, Serum amyloid P-component, Somatotropin, Stromal cell-derived factor 1, Thymic stromal lymphopoietin, Thyrotropin subunit beta, Transmembrane glycoprotein NMB, Tumor necrosis factor receptor superfamily member 8, Vascular endothelial growth factor D, Vascular endothelial growth factor receptor 1, Vascular endothelial growth factor receptor 2, Vascular endothelial growth factor receptor 3, and WAP four-disulfide core domain protein 2 (each referred to herein for convenience as a "stroke biomarker") can be used for diagnosis, prognosis, risk stratification, staging, monitoring, categorizing and determination of further diagnosis and treatment regimens in patients having or suspected of having a cerebral injury, including ischemic stroke, hemorrhagic stroke, TIA, or traumatic brain injury.

In a related aspect, the invention discloses methods for determining a diagnosis or prognosis related to cerebral injury, or for differentiating between types of strokes and/or TIA. As described herein, measurement of one or more of, preferably a plurality of, and most preferably each of, biomarkers selected from the group consisting of eotaxin, epidermal growth factor receptor, S100A12, TIMP-4, and prolactin (each referred to herein for convenience as a "stroke biomarker") can be used for diagnosis, prognosis, risk stratification, staging, monitoring, categorizing and determination of further diagnosis and treatment regimens in patients having or suspected of having a cerebral injury, including ischemic stroke, hemorrhagic stroke, TIA, or traumatic brain injury.

The stroke biomarkers of the present invention may be used, individually or in panels comprising a plurality of stroke biomarkers. The presence or amount of such marker(s) in a sample obtained from the subject can be used to rule in or rule out one or more of the following: traumatic brain injury, stroke, thrombotic stroke, embolic stroke, lacunar stroke, hypoperfusion, intracerebral hemorrhage, and subarachnoid hemorrhage, thereby either providing a diagnosis (rule-in) and/or excluding a diagnosis (rule-out).

As noted above, the present invention relates to methods for evaluating a stroke patient or a patient being evaluated for a possible diagnosis. These methods comprise performing an assay method that is configured to detect one or more biomarkers selected from the group consisting of Agouti-related protein, Alpha-2 macroglobulin, Alpha-fetoprotein, Amphiregulin, Angiopoietin-1 receptor, Angiopoietin-related protein 3, Angiopoietin-related protein 4, Angiopoietin-related protein 6, Bone morphogenetic protein 7, Cadherin-3, Cancer Antigen 15-3, Cancer Antigen 19-9, Carcinoembryonic antigen-related cell adhesion molecule 5, C—C motif chemokine 1, C—C motif chemokine 13, C—C motif chemokine 15, C—C motif chemokine 17, C—C motif chemokine 19, C—C motif chemokine 26, C—C motif chemokine 8, Choriogonadotropin subunit beta, Clusterin, C—X—C motif chemokine 11, C—X—C motif chemokine 6, C—X—C motif chemokine 9, Cyclin-dependent kinase inhibitor 1, Endoglin, Epiregulin, Epithelial cell adhesion molecule, Erythropoietin, Fatty acid-binding protein, liver, Fibroblast growth factor 19, Fibroblast growth factor 21, Fibroblast growth factor 23, Follistatin, Follitropin subunit beta, Galectin-3, Glial cell line-derived neurotrophic factor, Heat shock protein beta-1, Heparin-binding EGF-like growth factor, Heparin-binding growth factor 1, Hepatitis A virus cellular receptor 1, Hepatocyte growth factor receptor, Insulin receptor substrate 1, Insulin-like growth factor-binding protein 1, Insulin-like growth factor-binding protein 2, Insulin-like growth factor-binding protein 4, Intercellular adhesion molecule 3, Interleukin-1 receptor type I, Interleukin-1 receptor type II, Interleukin-11, Interleukin-21, Interleukin-28A, Interleukin-29, Interleukin-33, Interleukin-4 receptor alpha chain, Interleukin-6 receptor subunit alpha, Interleukin-6 receptor subunit beta, Keratin, type I cytoskeletal 19 (aa311-367), Kit ligand, Lutropin subunit beta, Lymphotactin, Macrophage colony-stimulating factor 1, Matrilysin, Metalloproteinase inhibitor 4, Growth-regulated alpha, beta, and gamma proteins (total), Mucin-16, Neprilysin, Neuronal cell adhesion molecule, NF-kappa-B inhibitor alpha, Osteocalcin, Oxidized low-density lipoprotein receptor 1, Parathyroid hormone, Platelet endothelial cell adhesion molecule, Probetacellulin, Pro-interleukin-16, Prolactin, Proprotein convertase subtilisin/kexin type 9, Prostate-specific antigen, Protein NOV homolog, Protransforming growth factor alpha, Serum amyloid P-component, Somatotropin, Stromal cell-derived factor 1, Thymic stromal lymphopoietin, Thyrotropin subunit beta, Transmembrane glycoprotein NMB, Tumor necrosis factor receptor superfamily member 8, Vascular endothelial growth factor D, Vascular endothelial growth factor receptor 1, Vascular endothelial growth factor receptor 2, Vascular endothelial growth factor receptor 3, and WAP four-disulfide core domain protein 2, the results of which assay(s) is/are then correlated to the status of the patient.

The present invention also relates to methods for evaluating a stroke patient or a patient being evaluated for a possible diagnosis. These methods comprise performing an assay method that is configured to detect one or more of, preferably a plurality of, and most preferably each of, biomarkers selected from the group consisting of eotaxin, epidermal growth factor receptor, S100A12, TIMP-4, and prolactin, the results of which assay(s) is/are then correlated to the status of the patient.

This correlation to status may include one or more of the following: diagnosis of stroke; diagnosis of stroke and indication if an acute stroke has occurred; diagnosis of stroke and indication if an non-acute stroke has occurred; diagnosis of stroke, indication if an acute stroke has occurred, and indication if an non-acute stroke has occurred; diagnosis of stroke and indication if an ischemic stroke has occurred; diagnosis of stroke and indication if a hemorrhagic stroke has occurred; diagnosis of stroke, indication if an ischemic stroke has occurred and indication if a hemorrhagic stroke has occurred; diagnosis of stroke and prognosis of a subsequent adverse outcome; diagnosis of stroke and prognosis of a subsequent cerebral vasospasm; diagnosis of stroke, indication if a hemorrhagic stroke has occurred, prognosis of a subsequent cerebral vasospasm; indication if a traumatic brain injury has occurred; indication of a prognosis resulting from a cerebral injury selected from the group consisting of ischemic stroke, hemorrhagic stroke, TIA, and traumatic brain injury.

In certain embodiments, the methods for evaluating a patient described herein are methods for risk stratification of the patient; that is, assigning a likelihood of one or more future changes in health status to the patient. In these embodiments, the assay result(s) is/are correlated to one or more such future changes. A level or a change in level of one or more stroke biomarkers, which in turn is(are) associated with an increased probability of morbidity or death, is referred to as being "associated with an increased predisposition to an adverse outcome" in a patient. Preferred prognostic markers can predict the likelihood of the onset of delayed neurologic deficits in a patient after stroke or other cerebral injury, predict the likelihood of a subsequent stroke, or predict the likelihood of death.

In such risk stratification embodiments, preferably the likelihood or risk assigned is that an event of interest is more or less likely to occur within 180 days of the time at which the body fluid sample is obtained from the patient. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the stroke patient is equivalent to diagnosis of a current condition.

For a positive going marker, an increased likelihood of the occurrence of a diagnosis is assigned to the patient when the measured concentration is above the threshold (relative to the likelihood assigned when the measured concentration is below the threshold); alternatively, when the measured concentration is below the threshold, an increased likelihood of the nonoccurrence of a diagnosis may be assigned to the patient (relative to the likelihood assigned when the measured concentration is above the threshold). For a negative going marker, an increased likelihood of the occurrence of a diagnosis is assigned to the patient when the measured concentration is below the threshold (relative to the likelihood assigned when the measured concentration is above the threshold); alternatively, when the measured concentration is above the threshold, an increased likelihood of the non-occurrence of a diagnosis may be assigned to the patient (relative to the likelihood assigned when the measured concentration is below the threshold).

In certain embodiments, a biomarker or panel of biomarkers is correlated to a condition or disease by merely its presence or absence. In other embodiments, a threshold level of a diagnostic or prognostic indicator can be established, and the level of the indicator in a patient sample can simply be compared to the threshold level. A variety of methods may be used by the skilled artisan to arrive at a desired threshold value for use in these methods. For example, for a positive going marker the threshold value may be determined from a population of patients not having had a stroke by selecting a concentration representing the $75^{th}$, $85^{th}$, $90^{th}$, $95^{th}$, or $99^{th}$ percentile of a stroke biomarker or biomarkers measured in such "normal" patients. Alternatively, the threshold value may be determined from a "diseased" population of patients by selecting a concentration representing the $75^{th}$, $85^{th}$, $90^{th}$, $95^{th}$, or $99^{th}$ percentile of a biomarker or biomarkers measured in patients suffering from a stroke or other cerebral injury.

Alternatively, the threshold value may be determined from a "diseased" population of stroke patients having a predisposition for an outcome such as death, worsening disease, etc.), by selecting a concentration representing the $75^{th}$, $85^{th}$, $90^{th}$, $95^{th}$, or $99^{th}$ percentile of a biomarker or biomarkers measured in patients suffering from a stroke or other cerebral injury and who later suffered from the outcome of interest.

In another alternative, the threshold value may be determined from a prior measurement of a biomarker or biomarkers in the same patient; that is, a temporal change in the level of a biomarker or biomarkers in the same patient may be used to assign a diagnosis or a prognosis to the patient. For example, a diagnostic indicator may be determined at an initial time, and again at a second time. In such embodiments, an increase in the marker from the initial time to the second time may be diagnostic of a particular type of stroke, or a given prognosis.

The foregoing discussion is not meant to imply, however, that the stroke biomarkers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which has a particular disease (or which is predisposed to some outcome), and a "second" subpopulation which does not have the disease (or is not so predisposed) can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more stroke biomarkers, or a composite of such markers, may be treated as continuous variables. For example, any particular concentration can be converted into a corresponding probability of existing disease, of a future outcome for the stroke patient, or mortality, of a SIRS classification, etc.

In yet another alternative, a threshold that can provide an acceptable level of specificity and sensitivity in separating a population of stroke patients into "bins" such as a "first" subpopulation and a "second" subpopulation. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess a patient. For example, a "first" subpopulation identified by an existing disease, predisposition to a future outcome for the stroke patient, predisposition to mortality, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to stroke patients based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in disease status in comparison to someone in the first tertile. The third tertile is also assigned an odds ratio that is relative to that first tertile.

In certain embodiments, the assay method is an immunoassay. Antibodies for use in such assays will specifically bind a full length stroke biomarker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the stroke biomarker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the stroke patient selected from the group consisting of demographic information (e.g., weight, sex, age, race), medical history (e.g., family history, type of surgery, pre-existing disease such as aneurism, congestive heart failure, diabetes mellitus, hypertension, coronary artery disease, proteinuria, or renal insufficiency, clinical variables (e.g., blood pressure, temperature, respiration rate), risk scores (APACHE score, PREDICT score, TIMI Risk Score for UA/NSTEMI, Framingham Risk Score), Essen Stroke Risk Score, California risj score, ABCD score, or ABCD2 score. This list is not meant to be limiting.

When more than one marker is measured, the individual markers may be measured in samples obtained at the same time, or may be determined from samples obtained at different (e.g., an earlier or later) times. The individual markers may also be measured on the same or different body fluid samples. For example, one stroke biomarker may be measured in a serum or plasma sample and another stroke biomarker may be measured in a urine sample. In addition, assignment of a likelihood may combine an individual biomarker assay result with temporal changes in one or more additional variables.

In various related aspects, the present invention also relates to devices and kits for performing the methods described herein. Suitable kits comprise reagents sufficient for performing an assay for at least one of the described stroke biomarkers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc.

In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

DETAILED DESCRIPTION OF THE INVENTION

The present invention relates to methods and compositions for diagnosis, differential diagnosis, risk stratification, monitoring, classifying and determination of treatment regimens in patients diagnosed with, or at risk of, stroke or other cerebral injury. In various embodiments, a measured concentration of one or more biomarkers selected from the group consisting of Agouti-related protein, Alpha-2 macroglobulin, Alpha-fetoprotein, Amphiregulin, Angiopoietin-1 receptor, Angiopoietin-related protein 3, Angiopoietin-related protein 4, Angiopoietin-related protein 6, Bone morphogenetic protein 7, Cadherin-3, Cancer Antigen 15-3, Cancer Antigen 19-9, Carcinoembryonic antigen-related cell adhesion molecule 5, C—C motif chemokine 1, C—C motif chemokine 13, C—C motif chemokine 15, C—C motif chemokine 17, C—C motif chemokine 19, C—C motif chemokine 26, C—C motif chemokine 8, Choriogonadotropin subunit beta, Clusterin, C—X—C motif chemokine 11, C—X—C motif chemokine 6, C—X—C motif chemokine 9, Cyclin-dependent kinase inhibitor 1, Endoglin, Epiregulin, Epithelial cell adhesion molecule, Erythropoietin, Fatty acid-binding protein, liver, Fibroblast growth factor 19, Fibroblast growth factor 21, Fibroblast growth factor 23, Follistatin, Follitropin subunit beta, Galectin-3, Glial cell line-derived neurotrophic factor, Heat shock protein beta-1, Heparin-binding EGF-like growth factor, Heparin-binding growth factor 1, Hepatitis A virus cellular receptor 1, Hepatocyte growth factor receptor, Insulin receptor substrate 1, Insulin-like growth factor-binding protein 1, Insulin-like growth factor-binding protein 2, Insulin-like growth factor-binding protein 4, Intercellular adhesion molecule 3, Interleukin-1 receptor type I, Interleukin-1 receptor type II, Interleukin-11, Interleukin-21, Interleukin-28A, Interleukin-29, Interleukin-33, Interleukin-4 receptor alpha chain, Interleukin-6 receptor subunit alpha, Interleukin-6 receptor subunit beta, Keratin, type I cytoskeletal 19 (aa311-367), Kit ligand, Lutropin subunit beta, Lymphotactin, Macrophage colony-stimulating factor 1, Matrilysin, Metalloproteinase inhibitor 4, Growth-regulated alpha, beta, and gamma proteins (total), Mucin-16, Neprilysin, Neuronal cell adhesion molecule, NF-kappa-B inhibitor alpha, Osteocalcin, Oxidized low-density lipoprotein receptor 1, Parathyroid hormone, Platelet endothelial cell adhesion molecule, Probetacellulin, Pro-interleukin-16, Prolactin, Proprotein convertase subtilisin/kexin type 9, Prostate-specific antigen, Protein NOV homolog, Protransforming growth factor alpha, Serum amyloid P-component, Somatotropin, Stromal cell-derived factor 1, Thymic stromal lymphopoietin, Thyrotropin subunit beta, Transmembrane glycoprotein NMB, Tumor necrosis factor receptor superfamily member 8, Vascular endothelial growth factor D, Vascular endothelial growth factor receptor 1, Vascular endothelial growth factor receptor 2, Vascular endothelial growth factor receptor 3, and WAP four-disulfide core domain protein 2 or one or more markers related thereto, are correlated to the status of the patient. As described herein, measurement of one or more biomarkers of the present invention may be used, individually or in panels comprising a plurality of biomarkers, in methods and compositions for the diagnosis, prognosis, or differentiation of stroke or other cerebral injury in a subject. Such markers can be used in diagnosing and treating a subject and/or to monitor the course of a treatment regimen; for screening subjects for the occurrence or risk of a particular disease; and for screening compounds and pharmaceutical compositions that might provide a benefit in treating or preventing such conditions.

For purposes of this document, the following definitions apply:

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology. A "stroke patient" is a patient suffering from stroke. Stroke patients may be further classified as having a specific type of stroke (e.g., thrombotic, embolic, lacunar, hypoperfusion, intracerebral hemorrhage, and sub arachnoid hemorrhage types of strokes. A "traumatic brain injury" patient is a patient for which an external force has traumatically injured the brain. Traumatic brain injury can be caused by a direct impact or by acceleration alone.

For purposes of this disclosure, the "acute" phase of a cerebral injury refers to up to 72 hours following the injury; "subacute" phase begins 3 days after the injury to 21 days after injury; and "chronic" phase begins after 21 days. For purposes of diagnosis, patients are preferably evaluated during the acute phase. For purposes of prognosis, patients may be evaluated during any of these three phases.

Specific neurologic dysfunctions or "stroke-associated symptoms" may include, but are not limited to, pain, headache, aphasia, apraxia, agnosia, amnesia, stupor, confusion, vertigo, coma, delirium, dementia, seizure, migraine insomnia, hypersomnia, sleep apnea, tremor, dyskinesia, paralysis, visual disturbances, diplopia, paresthesias, dysarthria, hemiplegia, hemianesthesia, hemianopia, etc. Patients exhibiting one or more of these symptoms but that have not suffered from a stroke are referred to herein as "stroke mimics".

Conditions within the differential diagnosis of stroke include brain tumor (including primary and metastatic disease), aneurysm, electrocution, burns, infections (e.g., meningitis), cerebral hypoxia, head injury (including concussion), stress, dehydration, nerve palsy (cranial or peripheral), hypoglycemia, migraine, multiple sclerosis, peripheral vascular disease, peripheral neuropathy, seizure (including grand mal seizure), subdural hematoma, syncope, and transient unilateral weakness. Preferred markers and marker panels are those that can distinguish stroke or traumatic brain injury from these stroke mimicking conditions.

Preferably, an analyte such as a stroke biomarker is measured in a sample. Such a sample may be obtained from a patient, such as a stroke patient. Preferred samples are body fluid samples.

The term "body fluid sample" as used herein refers to a sample of bodily fluid obtained for the purpose of diagnosis, prognosis, classification or evaluation of a stroke patient of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a stroke biomarker of the present invention, optionally together with other clinical characteristics, to arrive at a diagnosis (that is, the occurrence or nonoccurrence) of a disease or condition. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the stroke patient relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity or mortality is referred to as being "indicative of an increased likelihood" of an adverse outcome in a patient.

As used herein, the term "relating a signal to the presence or amount" of an analyte reflects the following understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the stroke biomarkers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting. With regard to biomarkers which exist in one form as type-I, type-II, or GPI-anchored membrane proteins, such membrane proteins typically comprise a substantial extracellular domain, some or all of which can be detected as soluble forms present in aqueous samples such as blood, serum, plasma, urine, etc., either as cleavage products or as splice variants which delete an effective membrane spanning domain. Preferred assays detect soluble forms of these biomarkers.

The term "positive going" marker as that term is used herein refer to a marker that is determined to be elevated in patients suffering from a disease or condition, relative to stroke not suffering from that disease or condition. The term "negative going" marker as that term is used herein refer to a marker that is determined to be reduced in patients suffering from a disease or condition, relative to patients not suffering from that disease or condition.

Stroke Biomarkers

The following table provides a list of the biomarkers of the present invention, together with the Swiss-Prot entry number for the human precursor. As noted above, these biomarkers are referred to for convenience as "stroke biomarkers," although they may be used as described herein with regard to non-stroke conditions such as traumatic brain injury.

| SwissProtNum | Preferred Name |
| --- | --- |
| O00253 | Agouti-related protein |
| P01023 | Alpha-2 macroglobulin |
| P02771 | Alpha-fetoprotein |
| P15514 | Amphiregulin |
| Q02763 | Angiopoietin-1 receptor |
| Q9Y5C1 | Angiopoietin-related protein 3 |
| Q9BY76 | Angiopoietin-related protein 4 |
| Q8NI99 | Angiopoietin-related protein 6 |
| P18075 | Bone morphogenetic protein 7 |
| P22223 | Cadherin-3 |
| P15941 | Cancer Antigen 15-3 |
| na | Cancer Antigen 19-9 |
| P06731 | Carcinoembryonic antigen-related cell adhesion molecule 5 |
| P22362 | C-C motif chemokine 1 |
| Q99616 | C-C motif chemokine 13 |
| Q16663 | C-C motif chemokine 15 |
| Q92583 | C-C motif chemokine 17 |
| Q99731 | C-C motif chemokine 19 |
| Q9Y258 | C-C motif chemokine 26 |
| P80075 | C-C motif chemokine 8 |
| P01233 | Choriogonadotropin subunit beta |
| P10909 | Clusterin |
| O14625 | C-X-C motif chemokine 11 |
| P80162 | C-X-C motif chemokine 6 |
| Q07325 | C-X-C motif chemokine 9 |
| P38936 | Cyclin-dependent kinase inhibitor 1 |
| P17813 | Endoglin |
| O14944 | Epiregulin |
| P16422 | Epithelial cell adhesion molecule |
| P01588 | Erythropoietin |
| P07148 | Fatty acid-binding protein, liver |
| O95750 | Fibroblast growth factor 19 |
| Q9NSA1 | Fibroblast growth factor 21 |
| Q9GZV9 | Fibroblast growth factor 23 |
| P19883 | Follistatin |
| P01225 | Follitropin subunit beta |
| P17931 | Galectin-3 |

-continued

| SwissProtNum | Preferred Name |
|---|---|
| P39905 | Glial cell line-derived neurotrophic factor |
| P04792 | Heat shock protein beta-1 |
| Q99075 | Heparin-binding EGF-like growth factor |
| P05230 | Heparin-binding growth factor 1 |
| Q96D42 | Hepatitis A virus cellular receptor 1 |
| P08581 | Hepatocyte growth factor receptor |
| P35568 | Insulin receptor substrate 1 |
| P08833 | Insulin-like growth factor-binding protein 1 |
| P18065 | Insulin-like growth factor-binding protein 2 |
| P22692 | Insulin-like growth factor-binding protein 4 |
| P32942 | Intercellular adhesion molecule 3 |
| P14778 | Interleukin-1 receptor type I |
| P27930 | Interleukin-1 receptor type II |
| P20809 | Interleukin-11 |
| Q9HBE4 | Interleukin-21 |
| Q8IZJ0 | Interleukin-28A |
| Q8IU54 | Interleukin-29 |
| O95760 | Interleukin-33 |
| P24394 | Interleukin-4 receptor alpha chain |
| P08887 | Interleukin-6 receptor subunit alpha |
| P40189 | Interleukin-6 receptor subunit beta |
| P08727 | Keratin, type I cytoskeletal 19 (aa311-367) |
| P21583 | Kit ligand |
| P01229 | Lutropin subunit beta |
| P47992 | Lymphotactin |
| P09603 | Macrophage colony-stimulating factor 1 |
| P09237 | Matrilysin |
| Q99727 | Metalloproteinase inhibitor 4 |
| P09341 | Growth-regulated alpha, beta, and gamma proteins (total) |
| P19875 | |
| P19876 | |
| Q8WXI7 | Mucin-16 |
| P08473 | Neprilysin |
| Q92823 | Neuronal cell adhesion molecule |
| P25963 | NF-kappa-B inhibitor alpha |
| P02818 | Osteocalcin |
| P78380 | Oxidized low-density lipoprotein receptor 1 |
| P01270 | Parathyroid hormone |
| P16284 | Platelet endothelial cell adhesion molecule |
| P35070 | Probetacellulin |
| Q14005 | Pro-interleukin-16 |
| P01236 | Prolactin |
| Q8NBP7 | Proprotein convertase subtilisin/kexin type 9 |
| P07288 | Prostate-specific antigen |
| P48745 | Protein NOV homolog |
| P01135 | Protransforming growth factor alpha |
| P02743 | Serum amyloid P-component |
| P01241 | Somatotropin |
| P48061 | Stromal cell-derived factor 1 |
| Q969D9 | Thymic stromal lymphopoietin |
| P01222 | Thyrotropin subunit beta |
| Q14956 | Transmembrane glycoprotein NMB |
| P28908 | Tumor necrosis factor receptor superfamily member 8 |
| O43915 | Vascular endothelial growth factor D |
| P17948 | Vascular endothelial growth factor receptor 1 |
| P35968 | Vascular endothelial growth factor receptor 2 |
| P35916 | Vascular endothelial growth factor receptor 3 |
| Q14508 | WAP four-disulfide core domain protein 2 |

The following table provides an additional list of the biomarkers of the present invention, together with the Swiss-Prot entry number for the human precursor. As noted above, these biomarkers are referred to for convenience as "stroke biomarkers," although they may be used as described herein with regard to non-stroke conditions such as traumatic brain injury.

| Preferred Name | SwissProt Entry |
|---|---|
| Eotaxin | P51671 |
| Epidermal growth factor receptor | P00533 |
| S100A12 | P80511 |
| Metalloproteinase inhibitor 4 (TIMP-4) | Q99727 |
| Prolactin | P01236 |

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and The Immunoassay Handbook, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described stroke biomarkers. The kit comprises reagents for the analysis of at least one test sample which comprise at least one antibody that binds a stroke biomarker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies bind a stroke biomarker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a stroke biomarker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ M$^{-1}$, and preferably between about $10^8$ M$^{-1}$ to about $10^9$ M$^{-1}$, about $10^9$ M$^{-1}$ to about $10^{10}$ M$^{-1}$, or about $10^{10}$ M$^{-1}$ to about $10^{12}$ M$^{-1}$.

Affinity is calculated as $K_d = k_{on}/k_{off}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides can confer improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a patient belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Additional clinical indicia may be combined with the stroke biomarker assay result(s) of the present invention. Other clinical indicia which may be combined with the stroke biomarker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, or renal insufficiency), risk scores (APACHE score, PREDICT score, TIMI Risk Score for UA/NSTEMI, Framingham Risk Score), etc.

Combining assay results/clinical indicia in this manner can comprise the use of multivariate logistical regression, loglinear modeling, neural network analysis, n-of-m analysis, decision tree analysis, etc. This list is not meant to be limiting.

Selecting a Treatment Regimen

Once a diagnosis is obtained, the clinician can readily select a treatment regimen that is compatible with the diagnosis. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Immunoassay Format

Analytes are measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

A list of the markers tested, with the associated Swiss-Prot entry number for the marker precursor and the units of measurement, is provided in the following table:

TABLE 1

| | | |
|---|---|---|
| O00253 | Agouti-related protein | ng/ml |
| P01023 | Alpha-2 macroglobulin | mg/mL |
| P02771 | Alpha-fetoprotein | ng/mL |
| P15514 | Amphiregulin | pg/ml |
| Q02763 | Angiopoietin-1 receptor | ng/ml |
| Q9Y5C1 | Angiopoietin-related protein 3 | ng/ml |
| Q9BY76 | Angiopoietin-related protein 4 | ng/ml |
| Q8NI99 | Angiopoietin-related protein 6 | ng/ml |
| P18075 | Bone morphogenetic protein 7 | pg/ml |
| P22223 | Cadherin-3 | ng/ml |
| P15941 | Cancer Antigen 15-3 | U/ml |
| na | Cancer Antigen 19-9 | U/mL |
| P06731 | Carcinoembryonic antigen-related cell adhesion molecule 5 | ng/mL |
| P22362 | C-C motif chemokine 1 | pg/ml |
| Q99616 | C-C motif chemokine 13 | pg/ml |
| Q16663 | C-C motif chemokine 15 | pg/ml |
| Q92583 | C-C motif chemokine 17 | pg/ml |
| Q99731 | C-C motif chemokine 19 | pg/ml |
| Q9Y258 | C-C motif chemokine 26 | pg/ml |
| P80075 | C-C motif chemokine 8 | pg/ml |
| P01233 | Choriogonadotropin subunit beta | mU/ml |
| P10909 | Clusterin | ng/mL |
| O14625 | C-X-C motif chemokine 11 | pg/ml |
| P80162 | C-X-C motif chemokine 6 | pg/ml |
| Q07325 | C-X-C motif chemokine 9 | pg/ml |
| P38936 | Cyclin-dependent kinase inhibitor 1 | pg/ml |
| P17813 | Endoglin | ng/ml |
| O14944 | Epiregulin | pg/ml |
| P16422 | Epithelial cell adhesion molecule | pg/ml |
| P01588 | Erythropoietin | pg/mL |
| P07148 | Fatty acid-binding protein, liver | ng/ml |
| O95750 | Fibroblast growth factor 19 | ng/ml |
| Q9NSA1 | Fibroblast growth factor 21 | ng/ml |
| Q9GZV9 | Fibroblast growth factor 23 | ng/ml |
| P19883 | Follistatin | pg/ml |
| P01225 | Follitropin subunit beta | mIU/mL |
| P17931 | Galectin-3 | ng/ml |
| P39905 | Glial cell line-derived neurotrophic | pg/ml |

TABLE 1-continued

| | factor | |
|---|---|---|
| P04792 | Heat shock protein beta-1 | ng/ml |
| Q99075 | Heparin-binding EGF-like growth factor | pg/ml |
| P05230 | Heparin-binding growth factor 1 | pg/ml |
| Q96D42 | Hepatitis A virus cellular receptor 1 | pg/ml |
| P08581 | Hepatocyte growth factor receptor | pg/ml |
| P35568 | Insulin receptor substrate 1 | ng/ml |
| P08833 | Insulin-like growth factor-binding protein 1 | ng/ml |
| P18065 | Insulin-like growth factor-binding protein 2 | ng/ml |
| P22692 | Insulin-like growth factor-binding protein 4 | ng/ml |
| P32942 | Intercellular adhesion molecule 3 | ng/ml |
| P14778 | Interleukin-1 receptor type I | pg/mL |
| P27930 | Interleukin-1 receptor type II | pg/ml |
| P20809 | Interleukin-11 | pg/ml |
| Q9HBE4 | Interleukin-21 | pg/ml |
| Q8IZJ0 | Interleukin-28A | pg/ml |
| Q8IU54 | Interleukin-29 | pg/ml |
| O95760 | Interleukin-33 | pg/ml |
| P24394 | Interleukin-4 receptor alpha chain | pg/ml |
| P08887 | Interleukin-6 receptor subunit alpha | pg/ml |
| P40189 | Interleukin-6 receptor subunit beta | pg/ml |
| P08727 | Keratin, type I cytoskeletal 19 (aa311-367) | pg/ml |
| P21583 | Kit ligand | pg/mL |
| P01229 | Lutropin subunit beta | mIU/mL |
| P47992 | Lymphotactin | ng/mL |
| P09603 | Macrophage colony-stimulating factor 1 | pg/ml |
| P09237 | Matrilysin | pg/ml |
| Q99727 | Metalloproteinase inhibitor 4 | pg/ml |
| P09341 P19875 | Growth-regulated alpha, beta, | pg/ml |
| P19876 | and gamma proteins (total) | |
| Q8WXI7 | Mucin-16 | U/mL |
| P08473 | Neprilysin | ng/ml |
| Q92823 | Neuronal cell adhesion molecule | pg/ml |
| P25963 | NF-kappa-B inhibitor alpha | ng/ml |
| P02818 | Osteocalcin | pg/ml |
| P78380 | Oxidized low-density lipoprotein receptor 1 | pg/ml |
| P01270 | Parathyroid hormone | pg/ml |
| P16284 | Platelet endothelial cell adhesion molecule | ng/ml |
| P35070 | Probetacellulin | pg/ml |
| Q14005 | Pro-interleukin-16 | pg/mL |
| P01236 | Prolactin | pg/ml |
| Q8NBP7 | Proprotein convertase subtilisin/kexin type 9 | pg/ml |
| P07288 | Prostate-specific antigen | ng/mL |
| P48745 | Protein NOV homolog | pg/ml |
| P01135 | Protransforming growth factor alpha | pg/ml |
| P02743 | Serum amyloid P-component | ug/mL |
| P01241 | Somatotropin | ng/mL |
| P48061 | Stromal cell-derived factor 1 | pg/ml |
| Q969D9 | Thymic stromal lymphopoietin | pg/ml |
| P01222 | Thyrotropin subunit beta | uIU/ml |
| Q14956 | Transmembrane glycoprotein NMB | ng/ml |
| P28908 | Tumor necrosis factor receptor superfamily member 8 | pg/ml |
| O43915 | Vascular endothelial growth factor D | pg/ml |
| P17948 | Vascular endothelial growth factor receptor 1 | pg/ml |
| P35968 | Vascular endothelial growth factor receptor 2 | pg/ml |
| P35916 | Vascular endothelial growth factor receptor 3 | pg/ml |
| Q14508 | WAP four-disulfide core domain protein 2 | pg/ml |

Example 2

Use of Analyte as a Marker for Assessing Patients for Stroke and/or TIA

Patients from the emergency department (ED) were classified as stroke mimics, positive for transient ischemic attack, positive for ischemic stroke, or positive for hemorrhagic stroke, in each case according to clinical diagnosis at the study site.

Two cohorts were defined as Cohort 1 and Cohort 2 as described in the following data tables. Plasma samples from each patient in Cohorts 1 and 2 were collected at enrollment. The concentrations of the analyte in these samples were measured by standard immunoassay methods using commercially available assay reagents. A receiver operating characteristic (ROC) curve was generated using the concentrations, and the performance of the analyte is assessed by the area under the ROC curve (AUC). The two-tailed p-value of the AUC for the analyte was also calculated to determine statistical significance. "Inc/Dec" indicates if the marker is increasing or decreasing in Cohort 1 relative to Cohort 2.

TABLE 2

Ischemic stroke + TIA (Cohort 1) vs. Mimics (Cohort 2)

| Marker Name | p | Inc/Dec | AUC |
|---|---|---|---|
| Agouti-related protein | 0.057 | Inc | 0.538 |
| Alpha-2 macroglobulin | 0.0502 | Dec | 0.663 |
| Alpha-fetoprotein | 0.0583 | Dec | 0.518 |
| Amphiregulin | 0.056 | Dec | 0.51 |
| Angiopoietin-1 receptor | 0.0559 | Inc | 0.509 |
| Angiopoietin-related protein 3 | 0.0578 | Dec | 0.511 |
| Angiopoietin-related protein 4 | 0.0568 | Inc | 0.548 |
| Angiopoietin-related protein 6 | 0.0528 | Dec | 0.637 |
| Bone morphogenetic protein 7 | 0.0557 | Dec | 0.521 |
| Cadherin-3 | 0.0549 | Dec | 0.549 |
| Cancer Antigen 15-3 | 0.052 | Dec | 0.659 |
| Cancer Antigen 19-9 | 0.0565 | Dec | 0.574 |
| Carcinoembryonic antigen-related cell adhesion molecule 5 | 0.0578 | Inc | 0.534 |
| C-C motif chemokine 1 | 0.0631 | Inc | 0.552 |
| C-C motif chemokine 13 | 0.0459 | Dec | 0.725 |
| C-C motif chemokine 15 | 0.0617 | Dec | 0.598 |
| C-C motif chemokine 17 | 0.0516 | Dec | 0.64 |
| C-C motif chemokine 19 | 0.0548 | Dec | 0.597 |
| C-C motif chemokine 26 | 0.0634 | Dec | 0.543 |
| C-C motif chemokine 8 | 0.064 | Dec | 0.508 |
| Choriogonadotropin subunit beta | 0.0522 | Inc | 0.656 |
| Clusterin | 0.056 | Dec | 0.502 |
| C-X-C motif chemokine 11 | 0.0577 | Dec | 0.513 |
| C-X-C motif chemokine 6 | 0.0579 | Dec | 0.503 |
| C-X-C motif chemokine 9 | 0.0573 | Dec | 0.529 |
| Cyclin-dependent kinase inhibitor 1 | 0.0496 | Inc | 0.665 |
| Endoglin | 0.056 | Inc | 0.501 |
| Epiregulin | 0.0547 | Dec | 0.561 |
| Epithelial cell adhesion molecule | 0.0556 | Dec | 0.524 |
| Erythropoietin | 0.0551 | Inc | 0.542 |
| Fatty acid-binding protein, liver | 0.0575 | Dec | 0.524 |
| Fibroblast growth factor 19 | 0.0579 | Dec | 0.508 |
| Fibroblast growth factor 21 | 0.0571 | Dec | 0.538 |
| Fibroblast growth factor 23 | 0.0568 | Dec | 0.547 |
| Follistatin | 0.0467 | Inc | 0.707 |
| Follitropin subunit beta | 0.055 | Dec | 0.593 |
| Galectin-3 | 0.0553 | Dec | 0.535 |
| Glial cell line-derived neurotrophic factor | 0.0636 | Dec | 0.514 |
| Heat shock protein beta-1 | 0.0532 | Inc | 0.597 |
| Heparin-binding EGF-like growth factor | 0.056 | Dec | 0.508 |
| Heparin-binding growth factor 1 | 0.0555 | Inc | 0.528 |
| Hepatitis A virus cellular receptor 1 | 0.0559 | Dec | 0.51 |
| Hepatocyte growth factor receptor | 0.0541 | Dec | 0.573 |
| Insulin receptor substrate 1 | 0.0501 | Inc | 0.656 |
| Insulin-like growth factor-binding protein 1 | 0.056 | Inc | 0.506 |
| Insulin-like growth factor-binding protein 2 | 0.0537 | Inc | 0.583 |
| Insulin-like growth factor-binding protein 4 | 0.0557 | Inc | 0.519 |
| Intercellular adhesion molecule 3 | 0.0514 | Dec | 0.658 |
| Interleukin-1 receptor type I | 0.0512 | Dec | 0.663 |
| Interleukin-1 receptor type II | 0.0557 | Dec | 0.576 |

TABLE 2-continued

Ischemic stroke + TIA (Cohort 1) vs. Mimics (Cohort 2)

| Marker Name | p | Inc/Dec | AUC |
|---|---|---|---|
| Interleukin-11 | 0.0573 | Inc | 0.529 |
| Interleukin-21 | 0.0633 | Inc | 0.546 |
| Interleukin-28A | 0.0634 | Dec | 0.54 |
| Interleukin-29 | 0.0576 | Inc | 0.513 |
| Interleukin-33 | 0.064 | Dec | 0.501 |
| Interleukin-4 receptor alpha chain | 0.0534 | Inc | 0.625 |
| Interleukin-6 receptor subunit alpha | 0.0531 | Dec | 0.63 |
| Interleukin-6 receptor subunit beta | 0.0517 | Dec | 0.654 |
| Keratin, type I cytoskeletal 19 (aa311-367) | 0.0562 | Inc | 0.58 |
| Kit ligand | 0.0619 | Dec | 0.591 |
| Lutropin subunit beta | 0.0539 | Dec | 0.616 |
| Lymphotactin | 0.0555 | Inc | 0.581 |
| Macrophage colony-stimulating factor 1 | 0.0573 | Dec | 0.527 |
| Matrilysin | 0.0558 | Inc | 0.52 |
| Metalloproteinase inhibitor 4 | 0.0566 | Inc | 0.538 |
| Mix of Growth-regulated alpha, beta, and gamma proteins | 0.063 | Inc | 0.537 |
| Mucin-16 | 0.0575 | Inc | 0.544 |
| Neprilysin | 0.0549 | Inc | 0.551 |
| Neuronal cell adhesion molecule | 0.0543 | Dec | 0.569 |
| NF-kappa-B inhibitor alpha | 0.0538 | Inc | 0.581 |
| Osteocalcin | 0.0565 | Dec | 0.556 |
| Oxidized low-density lipoprotein receptor 1 | 0.0633 | Dec | 0.515 |
| Parathyroid hormone | 0.057 | Dec | 0.537 |
| Platelet endothelial cell adhesion molecule | 0.0535 | Inc | 0.59 |
| Probetacellulin | 0.055 | Dec | 0.548 |
| Pro-interleukin-16 | 0.0624 | Dec | 0.578 |
| Prolactin | 0.0539 | Dec | 0.629 |
| Proprotein convertase subtilisin/kexin type 9 | 0.0554 | Dec | 0.534 |
| Prostate-specific antigen | 0.0559 | Inc | 0.588 |
| Protein NOV homolog | 0.0561 | Inc | 0.501 |
| Protransforming growth factor alpha | 0.0542 | Dec | 0.572 |
| Serum amyloid P-component | 0.0509 | Dec | 0.652 |
| Somatotropin | 0.0562 | Inc | 0.564 |
| Stromal cell-derived factor 1 | 0.0616 | Dec | 0.6 |
| Thymic stromal lymphopoietin | 0.064 | Dec | 0.507 |
| Thyrotropin subunit beta | 0.0569 | Dec | 0.543 |
| Transmembrane glycoprotein NMB | 0.0536 | Inc | 0.586 |
| Tumor necrosis factor receptor superfamily member 8 | 0.0569 | Dec | 0.541 |
| Vascular endothelial growth factor D | 0.0529 | Dec | 0.604 |
| Vascular endothelial growth factor receptor 1 | 0.0529 | Dec | 0.635 |
| Vascular endothelial growth factor receptor 2 | 0.0495 | Dec | 0.688 |
| Vascular endothelial growth factor receptor 3 | 0.0552 | Dec | 0.589 |
| WAP four-disulfide core domain protein 2 | 0.0533 | Inc | 0.638 |

TABLE 3

Ischemic stroke (Cohort 1) vs. Mimics + TIA (Cohort 2)

| Marker Name | p | Inc/Dec | AUC |
|---|---|---|---|
| Agouti-related protein | 0.9584 | Dec | 0.503 |
| Alpha-2 macroglobulin | 0.0088 | Dec | 0.631 |
| Alpha-fetoprotein | 0.3801 | Inc | 0.545 |
| Amphiregulin | 0.3556 | Inc | 0.547 |
| Angiopoietin-1 receptor | 0.7045 | Inc | 0.519 |
| Angiopoietin-related protein 3 | 0.8477 | Inc | 0.51 |
| Angiopoietin-related protein 4 | 0.0435 | Inc | 0.602 |
| Angiopoietin-related protein 6 | 0.0822 | Dec | 0.589 |
| Bone morphogenetic protein 7 | 0.4954 | Inc | 0.535 |
| Cadherin-3 | 0.3187 | Dec | 0.551 |
| Cancer Antigen 15-3 | 0.0373 | Inc | 0.606 |
| Cancer Antigen 19-9 | 0.552 | Dec | 0.531 |
| Carcinoembryonic antigen-related cell adhesion molecule 5 | 0.7858 | Dec | 0.514 |
| C-C motif chemokine 1 | 0.3197 | Inc | 0.567 |
| C-C motif chemokine 13 | 0.0019 | Dec | 0.654 |
| C-C motif chemokine 15 | 0.8491 | Dec | 0.513 |
| C-C motif chemokine 17 | 0.0015 | Dec | 0.657 |
| C-C motif chemokine 19 | 0.1684 | Dec | 0.57 |
| C-C motif chemokine 26 | 0.627 | Dec | 0.533 |
| C-C motif chemokine 8 | 0.974 | Dec | 0.502 |
| Choriogonadotropin subunit beta | 0.0442 | Inc | 0.602 |
| Clusterin | 0.5426 | Inc | 0.531 |
| C-X-C motif chemokine 11 | 0.6491 | Inc | 0.523 |
| C-X-C motif chemokine 6 | 0.3822 | Inc | 0.545 |
| C-X-C motif chemokine 9 | 0.6153 | Dec | 0.526 |
| Cyclin-dependent kinase inhibitor 1 | 0.0294 | Inc | 0.608 |
| Endoglin | 0.854 | Dec | 0.509 |
| Epiregulin | 0.8199 | Inc | 0.512 |
| Epithelial cell adhesion molecule | 0.5701 | Dec | 0.529 |
| Erythropoietin | 0.7817 | Dec | 0.514 |
| Fatty acid-binding protein, liver | 0.7862 | Dec | 0.514 |
| Fibroblast growth factor 19 | 0.638 | Inc | 0.524 |
| Fibroblast growth factor 21 | 0.8553 | Inc | 0.509 |
| Fibroblast growth factor 23 | 0.2176 | Dec | 0.563 |
| Follistatin | 0.0075 | Inc | 0.632 |
| Follitropin subunit beta | 0.7616 | Dec | 0.516 |
| Galectin-3 | 0.5639 | Inc | 0.529 |
| Glial cell line-derived neurotrophic factor | 0.4663 | Dec | 0.55 |
| Heat shock protein beta-1 | 0.101 | Inc | 0.583 |
| Heparin-binding EGF-like growth factor | 0.135 | Inc | 0.576 |
| Heparin-binding growth factor 1 | 0.7129 | Inc | 0.519 |
| Hepatitis A virus cellular receptor 1 | 0.9059 | Dec | 0.506 |
| Hepatocyte growth factor receptor | 0.7402 | Dec | 0.517 |
| Insulin receptor substrate 1 | 0.1939 | Inc | 0.566 |
| Insulin-like growth factor-binding protein 1 | 0.6237 | Inc | 0.525 |
| Insulin-like growth factor-binding protein 2 | 0.0247 | Inc | 0.612 |
| Insulin-like growth factor-binding protein 4 | 0.6447 | Inc | 0.523 |
| Intercellular adhesion molecule 3 | 0.1986 | Dec | 0.568 |
| Interleukin-1 receptor type I | 0.0454 | Dec | 0.601 |
| Interleukin-1 receptor type II | 0.1684 | Dec | 0.57 |
| Interleukin-11 | 0.1752 | Inc | 0.569 |
| Interleukin-21 | 0.1986 | Dec | 0.587 |
| Interleukin-28A | 0.0646 | Dec | 0.624 |
| Interleukin-29 | 0.7652 | Dec | 0.515 |
| Interleukin-33 | 0.6635 | Dec | 0.53 |
| Interleukin-4 receptor alpha chain | 0.1325 | Inc | 0.577 |
| Interleukin-6 receptor subunit alpha | 0.1357 | Dec | 0.576 |
| Interleukin-6 receptor subunit beta | 0.1831 | Dec | 0.568 |
| Keratin, type I cytoskeletal 19 (aa311-367) | 0.1982 | Inc | 0.566 |
| Kit ligand | 0.7703 | Inc | 0.52 |
| Lutropin subunit beta | 0.9094 | Dec | 0.506 |
| Lymphotactin | 0.701 | Inc | 0.52 |
| Macrophage colony-stimulating factor 1 | 0.6923 | Inc | 0.52 |
| Matrilysin | 0.5232 | Dec | 0.533 |
| Metalloproteinase inhibitor 4 | 0.0288 | Inc | 0.613 |
| Mix of Growth-regulated alpha, beta, and gamma proteins | 0.6613 | Inc | 0.53 |
| Mucin-16 | 0.7598 | Inc | 0.516 |
| Neprilysin | 0.2853 | Inc | 0.554 |
| Neuronal cell adhesion molecule | 0.3556 | Inc | 0.547 |
| NF-kappa-B inhibitor alpha | 0.4477 | Inc | 0.539 |
| Osteocalcin | 0.421 | Inc | 0.541 |
| Oxidized low-density lipoprotein receptor 1 | 0.6712 | Inc | 0.529 |
| Parathyroid hormone | 0.9811 | Inc | 0.501 |
| Platelet endothelial cell adhesion molecule | 0.6301 | Inc | 0.524 |
| Probetacellulin | 0.4352 | Dec | 0.54 |
| Pro-interleukin-16 | 0.9076 | Dec | 0.508 |
| Prolactin | 0.2906 | Dec | 0.555 |
| Proprotein convertase subtilisin/kexin type 9 | 0.8167 | Inc | 0.512 |
| Prostate-specific antigen | 0.0493 | Inc | 0.6 |
| Protein NOV homolog | 0.8168 | Dec | 0.512 |
| Protransforming growth factor alpha | 0.9379 | Dec | 0.505 |
| Serum amyloid P-component | 0.0606 | Dec | 0.596 |
| Somatotropin | 0.0857 | Inc | 0.587 |

TABLE 3-continued

Ischemic stroke (Cohort 1) vs. Mimics + TIA (Cohort 2)

| | | | |
|---|---|---|---|
| Stromal cell-derived factor 1 | 0.1301 | Dec | 0.602 |
| Thymic stromal lymphopoietin | 0.2869 | Dec | 0.572 |
| Thyrotropin subunit beta | 0.1617 | Dec | 0.571 |
| Transmembrane glycoprotein NMB | 0.4726 | Dec | 0.536 |
| Tumor necrosis factor receptor superfamily member 8 | 0.1409 | Dec | 0.575 |
| Vascular endothelial growth factor D | 0.4156 | Dec | 0.541 |
| Vascular endothelial growth factor receptor 1 | 0.0243 | Dec | 0.613 |
| Vascular endothelial growth factor receptor 2 | 0.033 | Dec | 0.607 |
| Vascular endothelial growth factor receptor 3 | 0.9207 | Dec | 0.505 |
| WAP four-disulfide core domain protein 2 | 0.122 | Inc | 0.579 |

TABLE 4

Ischemic stroke (Cohort 1) vs. Mimics (Cohort 2)

| | | | |
|---|---|---|---|
| Agouti-related protein | 0.0625 | Inc | 0.525 |
| Alpha-2 macroglobulin | 0.0551 | Dec | 0.684 |
| Alpha-fetoprotein | 0.0635 | Inc | 0.513 |
| Amphiregulin | 0.0613 | Inc | 0.514 |
| Angiopoietin-1 receptor | 0.0611 | Inc | 0.518 |
| Angiopoietin-related protein 3 | 0.0631 | Dec | 0.501 |
| Angiopoietin-related protein 4 | 0.0615 | Inc | 0.575 |
| Angiopoietin-related protein 6 | 0.0587 | Dec | 0.64 |
| Bone morphogenetic protein 7 | 0.0612 | Inc | 0.509 |
| Cadherin-3 | 0.0601 | Dec | 0.564 |
| Cancer Antigen 15-3 | 0.0576 | Dec | 0.666 |
| Cancer Antigen 19-9 | 0.0621 | Dec | 0.572 |
| Carcinoembryonic antigen-related cell adhesion molecule 5 | 0.0634 | Inc | 0.521 |
| C-C motif chemokine 1 | 0.0743 | Inc | 0.578 |
| C-C motif chemokine 13 | 0.0518 | Dec | 0.73 |
| C-C motif chemokine 15 | 0.0746 | Dec | 0.566 |
| C-C motif chemokine 17 | 0.055 | Dec | 0.685 |
| C-C motif chemokine 19 | 0.0599 | Dec | 0.609 |
| C-C motif chemokine 26 | 0.0749 | Dec | 0.548 |
| C-C motif chemokine 8 | 0.075 | Dec | 0.505 |
| Choriogonadotropin subunit beta | 0.057 | Inc | 0.676 |
| Clusterin | 0.0611 | Inc | 0.515 |
| C-X-C motif chemokine 11 | 0.0629 | Inc | 0.503 |
| C-X-C motif chemokine 6 | 0.0626 | Inc | 0.523 |
| C-X-C motif chemokine 9 | 0.0623 | Dec | 0.537 |
| Cyclin-dependent kinase inhibitor 1 | 0.0549 | Inc | 0.679 |
| Endoglin | 0.0613 | Dec | 0.5 |
| Epiregulin | 0.0609 | Dec | 0.541 |
| Epithelial cell adhesion molecule | 0.0608 | Dec | 0.536 |
| Erythropoietin | 0.061 | Inc | 0.521 |
| Fatty acid-binding protein, liver | 0.0628 | Dec | 0.525 |
| Fibroblast growth factor 19 | 0.063 | Inc | 0.512 |
| Fibroblast growth factor 21 | 0.0629 | Dec | 0.516 |
| Fibroblast growth factor 23 | 0.0616 | Inc | 0.57 |
| Follistatin | 0.0522 | Inc | 0.718 |
| Follitropin subunit beta | 0.0613 | Dec | 0.573 |
| Galectin-3 | 0.0612 | Dec | 0.504 |
| Glial cell line-derived neurotrophic factor | 0.0753 | Dec | 0.541 |
| Heat shock protein beta-1 | 0.0584 | Inc | 0.613 |
| Heparin-binding EGF-like growth factor | 0.0611 | Inc | 0.532 |
| Heparin-binding growth factor 1 | 0.0609 | Inc | 0.53 |
| Hepatitis A virus cellular receptor 1 | 0.0612 | Dec | 0.509 |
| Hepatocyte growth factor receptor | 0.0602 | Dec | 0.559 |
| Insulin receptor substrate 1 | 0.0569 | Inc | 0.645 |
| Insulin-like growth factor-binding protein 1 | 0.0611 | Inc | 0.516 |
| Insulin-like growth factor-binding protein 2 | 0.0579 | Inc | 0.624 |
| Insulin-like growth factor-binding protein 4 | 0.0609 | Inc | 0.527 |
| Intercellular adhesion molecule 3 | 0.0583 | Dec | 0.651 |
| Interleukin-1 receptor type I | 0.0563 | Dec | 0.675 |
| Interleukin-1 receptor type II | 0.0606 | Inc | 0.594 |
| Interleukin-11 | 0.0617 | Inc | 0.562 |
| Interleukin-21 | 0.075 | Dec | 0.54 |
| Interleukin-28A | 0.0735 | Dec | 0.609 |
| Interleukin-29 | 0.0629 | Inc | 0.501 |
| Interleukin-33 | 0.0751 | Dec | 0.519 |

TABLE 4-continued

Ischemic stroke (Cohort 1) vs. Mimics (Cohort 2)

| | | | |
|---|---|---|---|
| Interleukin-4 receptor alpha chain | 0.0584 | Inc | 0.641 |
| Interleukin-6 receptor subunit alpha | 0.0587 | Inc | 0.635 |
| Interleukin-6 receptor subunit beta | 0.057 | Dec | 0.665 |
| Keratin, type I cytoskeletal 19 (aa311-367) | 0.0612 | Inc | 0.596 |
| Kit ligand | 0.0749 | Dec | 0.541 |
| Lutropin subunit beta | 0.0609 | Dec | 0.586 |
| Lymphotactin | 0.0614 | Inc | 0.569 |
| Macrophage colony-stimulating factor 1 | 0.0628 | Dec | 0.51 |
| Matrilysin | 0.0613 | Dec | 0.501 |
| Metalloproteinase inhibitor 4 | 0.061 | Inc | 0.59 |
| Mix of Growth-regulated alpha, beta, and gamma proteins | 0.0745 | Inc | 0.538 |
| Mucin-16 | 0.063 | Inc | 0.54 |
| Neprilysin | 0.06 | Inc | 0.567 |
| Neuronal cell adhesion molecule | 0.061 | Dec | 0.524 |
| NF-kappa-B inhibitor alpha | 0.0596 | Inc | 0.582 |
| Osteocalcin | 0.0626 | Dec | 0.523 |
| Oxidized low-density lipoprotein receptor 1 | 0.0746 | Inc | 0.511 |
| Parathyroid hormone | 0.0625 | Dec | 0.526 |
| Platelet endothelial cell adhesion molecule | 0.0596 | Inc | 0.582 |
| Probetacellulin | 0.0614 | Dec | 0.512 |
| Pro-interleukin-16 | 0.0749 | Dec | 0.547 |
| Prolactin | 0.0597 | Dec | 0.63 |
| Proprotein convertase subtilisin/kexin type 9 | 0.061 | Dec | 0.52 |
| Prostate-specific antigen | 0.06 | Inc | 0.623 |
| Protein NOV homolog | 0.0613 | Inc | 0.502 |
| Protransforming growth factor alpha | 0.0606 | Dec | 0.555 |
| Serum amyloid P-component | 0.0564 | Dec | 0.662 |
| Somatotropin | 0.0604 | Inc | 0.597 |
| Stromal cell-derived factor 1 | 0.0723 | Dec | 0.638 |
| Thymic stromal lymphopoietin | 0.0748 | Dec | 0.551 |
| Thyrotropin subunit beta | 0.0613 | Dec | 0.574 |
| Transmembrane glycoprotein NMB | 0.0594 | Dec | 0.586 |
| Tumor necrosis factor receptor superfamily member 8 | 0.0616 | Dec | 0.563 |
| Vascular endothelial growth factor D | 0.0591 | Dec | 0.594 |
| Vascular endothelial growth factor receptor 1 | 0.0573 | Dec | 0.66 |
| Vascular endothelial growth factor receptor 2 | 0.0547 | Dec | 0.698 |
| Vascular endothelial growth factor receptor 3 | 0.0616 | Dec | 0.563 |
| WAP four-disulfide core domain protein 2 | 0.0587 | Inc | 0.649 |

TABLE 5

Ischemic stroke (Cohort 1) vs. Hemorrhagic stroke (Cohort 2)

| | | | |
|---|---|---|---|
| Agouti-related protein | 0.1385 | Dec | 0.594 |
| Alpha-2 macroglobulin | 0.7985 | Dec | 0.523 |
| Alpha-fetoprotein | 0.1983 | Inc | 0.583 |
| Amphiregulin | 0.6178 | Dec | 0.533 |
| Angiopoietin-1 receptor | 0.0202 | Inc | 0.644 |
| Angiopoietin-related protein 3 | 0.0095 | Inc | 0.661 |
| Angiopoietin-related protein 4 | 0.0515 | Inc | 0.623 |
| Angiopoietin-related protein 6 | 0.0002 | Inc | 0.721 |
| Bone morphogenetic protein 7 | 0.1847 | Inc | 0.584 |
| Cadherin-3 | 0.4399 | Dec | 0.549 |
| Cancer Antigen 15-3 | 0.0162 | Inc | 0.65 |
| Cancer Antigen 19-9 | 0.1691 | Inc | 0.588 |
| Carcinoembryonic antigen-related cell adhesion molecule 5 | 0.2414 | Dec | 0.575 |
| C-C motif chemokine 1 | 0.4566 | Inc | 0.636 |
| C-C motif chemokine 13 | 0.2668 | Dec | 0.698 |
| C-C motif chemokine 15 | 0.043 | Dec | 0.815 |
| C-C motif chemokine 17 | 0.6132 | Dec | 0.593 |
| C-C motif chemokine 19 | 0.0043 | Inc | 0.671 |
| C-C motif chemokine 26 | 0.4357 | Inc | 0.642 |
| C-C motif chemokine 8 | 0.7102 | Dec | 0.568 |
| Choriogonadotropin subunit beta | 0.694 | Inc | 0.525 |
| Clusterin | 0.1715 | Dec | 0.587 |

TABLE 5-continued

Ischemic stroke (Cohort 1) vs. Hemorrhagic stroke (Cohort 2)

| | | | |
|---|---|---|---|
| C-X-C motif chemokine 11 | 0.0532 | Dec | 0.62 |
| C-X-C motif chemokine 6 | 0.0846 | Dec | 0.607 |
| C-X-C motif chemokine 9 | 0.0242 | Inc | 0.638 |
| Cyclin-dependent kinase inhibitor 1 | 0.0101 | Dec | 0.659 |
| Endoglin | 0.1722 | Inc | 0.586 |
| Epiregulin | 0.2576 | Dec | 0.573 |
| Epithelial cell adhesion molecule | 0.2803 | Inc | 0.569 |
| Erythropoietin | 0.0001 | Inc | 0.724 |
| Fatty acid-binding protein, liver | 0.4918 | Inc | 0.544 |
| Fibroblast growth factor 19 | 0.0412 | Dec | 0.629 |
| Fibroblast growth factor 21 | 0.067 | Inc | 0.616 |
| Fibroblast growth factor 23 | <0.0001 | Inc | 0.735 |
| Follistatin | 0.1073 | Dec | 0.599 |
| Follitropin subunit beta | 0.2194 | Inc | 0.578 |
| Galectin-3 | 0.7541 | Inc | 0.52 |
| Glial cell line-derived neurotrophic factor | 0.3 | Dec | 0.686 |
| Heat shock protein beta-1 | 0.5681 | Dec | 0.537 |
| Heparin-binding EGF-like growth factor | 1 | Dec | 0.5 |
| Heparin-binding growth factor 1 | 0.521 | Inc | 0.54 |
| Hepatitis A virus cellular receptor 1 | 0.95 | Inc | 0.504 |
| Hepatocyte growth factor receptor | 0.3939 | Inc | 0.555 |
| Insulin receptor substrate 1 | 0.0293 | Dec | 0.637 |
| Insulin-like growth factor-binding protein 1 | 0.612 | Inc | 0.532 |
| Insulin-like growth factor-binding protein 2 | 0.2352 | Dec | 0.575 |
| Insulin-like growth factor-binding protein 4 | 0.0008 | Dec | 0.698 |
| Intercellular adhesion molecule 3 | 0.671 | Dec | 0.54 |
| Interleukin-1 receptor type I | 0.1784 | Inc | 0.586 |
| Interleukin-1 receptor type II | 0.2245 | Dec | 0.578 |
| Interleukin-11 | 0.4059 | Dec | 0.552 |
| Interleukin-21 | 0.043 | Dec | 0.815 |
| Interleukin-28A | 0.5897 | Dec | 0.599 |
| Interleukin-29 | 0.7651 | Inc | 0.519 |
| Interleukin-33 | 0.5439 | Dec | 0.611 |
| Interleukin-4 receptor alpha chain | 0.4688 | Inc | 0.547 |
| Interleukin-6 receptor subunit alpha | 0.0487 | Inc | 0.624 |
| Interleukin-6 receptor subunit beta | 0.0513 | Inc | 0.623 |
| Keratin, type I cytoskeletal 19 (aa311-367) | 0.8219 | Inc | 0.515 |
| Kit ligand | 0.8646 | Dec | 0.531 |
| Lutropin subunit beta | 0.0287 | Inc | 0.636 |
| Lymphotactin | 0.3335 | Dec | 0.561 |
| Macrophage colony-stimulating factor 1 | 0.5075 | Dec | 0.542 |
| Matrilysin | 0.0336 | Dec | 0.63 |
| Metalloproteinase inhibitor 4 | 0.3346 | Dec | 0.591 |
| Mix of Growth-regulated alpha, beta, and gamma proteins | 0.2838 | Dec | 0.691 |
| Mucin-16 | 0.0441 | Inc | 0.627 |
| Neprilysin | 0.0868 | Inc | 0.608 |
| Neuronal cell adhesion molecule | 0.0001 | Inc | 0.724 |
| NF-kappa-B inhibitor alpha | 0.7395 | Inc | 0.521 |
| Osteocalcin | 0.021 | Inc | 0.643 |
| Oxidized low-density lipoprotein receptor 1 | 0.661 | Dec | 0.58 |
| Parathyroid hormone | 0.2408 | Inc | 0.574 |
| Platelet endothelial cell adhesion molecule | 0.1419 | Inc | 0.591 |
| Probetacellulin | 0.4909 | Dec | 0.545 |
| Pro-interleukin-16 | 0.2503 | Dec | 0.704 |
| Prolactin | 0.0145 | Inc | 0.652 |
| Proprotein convertase subtilisin/kexin type 9 | 0.3576 | Dec | 0.557 |
| Prostate-specific antigen | 0.4945 | Inc | 0.544 |
| Protein NOV homolog | 0.2976 | Inc | 0.566 |
| Protransforming growth factor alpha | 0.3192 | Dec | 0.679 |
| Serum amyloid P-component | 0.8767 | Dec | 0.514 |
| Somatotropin | 0.95 | Dec | 0.504 |
| Stromal cell-derived factor 1 | 0.2187 | Dec | 0.716 |
| Thymic stromal lymphopoietin | 0.3952 | Dec | 0.654 |
| Thyrotropin subunit beta | 0.0185 | Inc | 0.645 |
| Transmembrane glycoprotein NMB | 0.0016 | Inc | 0.688 |
| Tumor necrosis factor receptor superfamily member 8 | 0.1871 | Dec | 0.584 |
| Vascular endothelial growth factor D | 0.0559 | Inc | 0.617 |
| Vascular endothelial growth factor receptor 1 | 0.8211 | Inc | 0.515 |
| Vascular endothelial growth factor receptor 2 | 0.3077 | Inc | 0.566 |
| Vascular endothelial growth factor receptor 3 | 0.193 | Dec | 0.583 |
| WAP four-disulfide core domain protein 2 | 0.7918 | Dec | 0.517 |

Example 3

Use of Analyte Panels for Assessing Patients for Stroke and/or TIA

Patients from the emergency department (ED) were enrolled in the study based on inclusion criteria consisting of: age > to 18 years, no recent history of trauma, having brain imaging performed, and experiencing a new neurologic symptom within 24 hours of blood draw. Exclusion criteria included hemoglobin <12.5 g/dL for females and 13.5 g/dL for males, untreated systolic blood pressure <90 mm Hg, and untreated diastolic blood pressure <50 mm Hg. Stroke was defined as a persistent neurological deficit in a logical vascular distribution lasting 1.) ≥24 hours or 2.) <24 hours but was either CT and/or MRI positive. Patients with a proven non-vascular condition and negative radiography interpreted by radiologists blinded to biomarker outcomes were stroke mimics Patients with neurologic findings lasting <24 hours in a logical vascular distribution, negative radiography, and negative workup for mimics were TIAs. Finally, those with intraparenchymal blood by radiograph were ICHs.

Plasma samples from each patient were collected at enrollment. The concentrations of the analyte in these samples were measured by standard immunoassay methods using commercially available assay reagents.

Statistical analysis was performed using SAS 9.3 (SAS, Cary, N.C.). Descriptive statistics were obtained for demographic and clinical variables in each pathologic group: ischemic stroke, intracranial hemorrhage (ICH), TIA, and mimic Means were compared across groups by one-way analysis of variance (ANOVA) tests if the variable was continuous and by $\chi^2$ tests if categorical.

Univariate logistic regressions were performed with each biomarker to predict the likelihood of stroke versus mimic, stroke versus TIA+mimic, stroke+TIA versus mimic, stroke versus ICH, and stroke+ICH versus mimic Biomarkers significant in univariate logistic regression in each group with a p-value ≤0.2 were retained and used to build multivariate logistic regression models within each comparison group. A stepwise selection method was employed to build the most parsimonious multivariate models maximizing predictive power and minimizing the number of covariates. Variables were retained if the F statistic was significant at p=0.05. The final variables were tested for multicollinearity by testing linear correlation (r>0.8) and variance inflation factor (>2.5). The area under the curve (AUC) of the receiver operating curve (ROC) of the models, captured by the concordance index or c-statistic, was used as a measure of the overall discriminative capacity of each model.

The stroke vs mimic model was set as a base model since the classification of both stroke and mimic patients was most rigorous, while the diagnosis of TIA was one of exclusion. Biomarker levels from a healthy cohort of subjects were a reference to test the discriminative capacity of the 3 variables to distinguish between patients with ischemic stroke and healthy patients. To internally validate this model, a SAS macro was adapted to bootstrap the parameter estimates and the c-statistic of the base model comparing ischemic stroke and mimics with 50 balanced re-samples generated.

In order to create one overall model, biomarkers significant in the multivariate models of ischemic stroke+TIA vs. mimic, ischemic stroke vs. TIA+mimic, ischemic stroke vs. ICH, and ischemic stroke+ICH vs mimic were added to the base model incrementally and changes in bootstrapped c-statistics were monitored in the ischemic stroke vs. mimic comparison. Biomarkers contributing at least 1 percent increase in the c-statistic were retained. The overall model was used to generate boostrapped parameter estimates and c-statistics for the following comparisons: ischemic stroke versus mimic, ischemic stroke versus ICH, and ischemic stroke+ICH versus mimic. Sensitivities, specificities, positive predictive values (PPV), and negative predictive values (NPV) were determined for the probability of each outcome at which sensitivity is maximized with specificity at least 50%. These statistics were calculated at 30%, the approximate prevalence of stroke among patients who present to emergency rooms, and at the probability of the outcome in this study sample.[30]

To test the robustness of this model in face of the diagnostic uncertainty of the TIA group, the bootstrapped parameter estimates and intercept of the stroke vs mimic comparison were used to predict TIA+stroke vs. mimic and stroke vs. TIA+mimic. Also, the model capacity to discriminate between anterior versus posterior and lacunar circulation ischemic strokes was also tested.

The predicted probabilities from the selected models were divided into deciles and the average predicted probability was plotted against the observed probability of patients within that decile. The distribution of predicted values yielded from inputting biomarker values of each patient into the model was plotted as a function of pathology.

Finally, the biomarkers of the base model were tested for collinearity (Pearson correlation >0.4) with demographic variables known at presentation including age, gender, and race by. These covariates were used to build multivariate models which were compared to the final model. Additionally, a boxplot of each of the 5 final biomarkers was created displaying the mean, median, and interquartile ranges of each biomarker as a function of pathology.

Table 6 depicts the demographic and health status characteristics of each pathology group. In this sample, the mean age was 64.4±15.2 years (range 26 to 92); the average age among patients within each pathologic groups was not significantly different at α=0.05 (p=0.0772). The percent of patients in the aggregate sample who were male and female were 50.3% (N=84) and 49.7% (N=83), respectively. The proportion of each gender was not significantly different by pathologic group (p=0.1416). Overall, there were 100 white patients (58.9%), 63 black patients (37.7%), and 4 of other race (2.4%). The proportion of patients in each pathologic group who were white in comparison to those who were black or other was significantly different by pathologic group (p=0.0153). Among those with ICH, blacks and people of other races were overrepresented.

In terms of co-morbidities, nearly 80% of patients had hypertension uniformly across all groups, 30% had diabetes mellitus, and about 30% had known hyperlipidemia. A history of prior stroke was not significantly different in any of the groups of patients. Only the proportion of patients with atrial fibrillation was higher in both the ischemic stroke and TIA groups (p=0.0263).

TABLE 6

| | Demographic and health status characteristics | | | | | |
|---|---|---|---|---|---|---|
| Characteristic | Ischemic Stroke N = 63 | ICH N = 26 | TIA N = 41 | Mimic N = 37 | Healthy Patients N = 70 | P-value |
| Age (mean, SD) | 67.1(15.3) | 63.7(14.0) | 63.05(15.9) | 61.8(15.0) | 44(16.0) | 0.0772 |
| Males | 35(55.6) | 16(61.5) | 20(48.8) | 13(35.1) | 42(59.2) | 0.1416 |
| Race | | | | | | 0.0153 |
| White | 40(63.5) | 9(34.6) | 30(73.2) | 21(56.8) | 49(69.0) | |
| Black + Other | 23(36.5) | 17(65.4) | 11(26.8) | 16(43.2) | 21(31.0) | |
| Comorbidities | | | | | | |
| Hypertension | 52(82.5) | 21(80.8) | 30(73.2) | 30(81.1) | — | 0.6932 |
| Diabetes mellitus | 18(28.6) | 7(26.9) | 14(34.2) | 14(37.8) | — | 0.7256 |
| Hyperlipidemia | 17(27.0) | 7(26.9) | 12(29.3) | 12(32.4) | — | 0.9426 |
| Atrial fibrillation | 12(19.1) | 0(0.0) | 8(19.5) | 2(5.4) | — | 0.0263 |
| Prior CVA/TIA | 17(27.0) | 11(42.3) | 13(31.7) | 12(32.4) | — | 0.5711 |
| Smoking | 17(27.0) | 2(7.7) | 9(22.0) | 7(18.9) | — | 0.2347 |
| Crack/Cocaine | 3(4.8) | 3(11.5) | 1(2.4) | 0(0.0) | — | 0.1400 |

Table 2 contains the most common symptoms at presentation which included new onset of motor weakness (64.07%), speech/language problems (53.9%), sensory numbness (36.53%), headache (28.74%), altered mental status (22.16%), and visual disturbances (19.16%). A greater proportion of patients with ischemic strokes and TIAs were affected by speech/language difficulty (p<0.0001). Patients with ICH were less likely to suffer from motor deficits the patients of other diagnoses, particularly ischemic stroke (p=0.0093). Sensory deficits were experienced less by ICH patients than by patients in the other groups (p=0.0126). Patients with TIAs were less likely to have a change in mental status than those with the other diagnoses (p<0.001 The overall average NIH stroke scale score was 5.1±6.4. Patients diagnosed with ischemic stroke and ICH scored higher than TIAs and mimics (p<0.0001). The average GCS was 14.2±2.1, and was particularly low among ICH and ischemic stroke patients (p=0.0018).

The median time from symptom onset to or last known usual state of health to serum biomarker blood draw was 10.25 hours (5, 18.75 interquartile range). Nearly 98% of patients received brain imaging which included CT, and 2% received MRI only. Among patients who had ischemic stroke, mimics, or TIA, 74 patients (44.1%) had a CT and an MRI. Among patients who had intracranial hemorrhage, 100% of patients had a CT.

The ABCD2 assessment and TOAST classification results are presented in Table 7 for patients diagnosed with TIAs and ischemic strokes, respectively. The ABCD2 score predicts the risk of a stroke within 90 days after the TIA based on multiple covariates.[31] The average ABCD2 score for this TIA sample was 4.39±1.16. The TOAST classification system is based on clinical symptoms and results from further investigation to determine the etiology of a stroke.[32] The majority of stroke events were due to an undetermined cause (41.3%) and secondary to atherosclerosis (33.3%), while 7% were due to a cardioembolic event. Among patients with ischemic strokes, nearly 57% occur in the anterior circulation, 11% comprise a lacunar infarct, and about 14% occur in the posterior circulation.

Multivariate logistic regression models built by stepwise selection from the pool of variables significant in the univariate analysis for each comparison group are displayed in Table 4. The log-odds of ischemic stroke versus mimic was predicted well by three biomarkers—eotaxin ($p=0.0005$), EGFR v1 ($p=0.0153$), and S100A12 ($p=0.0206$)—with a concordance index of 0.899. This model was used as the base model which was then bootstrapped for internal validation to obtain minimally biased parameter estimates and concordance statistics. The bootstrapped mean parameter estimates of the 3 aforementioned biomarkers comparing ischemic stroke versus mimic were the following: eotaxin ($\beta=0.0023$, $p=0.0016$), EGFR v1 ($\beta=0.0015$, $p=0.1107$), and S100A12 ($\beta=-0.0726$, $p=0.1174$). The bootstrapped mean concordance index was 0.8652.

The parameter estimates from this model were applied to predict the log-odds of being an ischemic stroke patient versus a healthy volunteer. When the coefficients were fixed to those of the ischemic stroke versus mimic model, the concordance index was 0.5 with a lack of fit ($p<0.0001$).

TABLE 7

Clinical and radiographic characteristics

| Characteristic | Ischemic Stroke N = 63 | ICH N = 26 | TIA N = 41 | Mimic N = 37 | P-value |
|---|---|---|---|---|---|
| Symptoms | | | | | |
| Speech/Language | 44(69.8) | 5(19.2) | 25(61.0) | 16(43.2) | <.0001 |
| Motor deficits | 50(79.4) | 12(46.2) | 23(56.1) | 22(59.5) | 0.0093 |
| Sensory deficits | 23(36.5) | 3(11.5) | 21(51.2) | 14(37.8) | 0.0126 |
| Visual deficits | 12(19.1) | 5(19.2) | 6(14.6) | 9(24.3) | 0.7578 |
| AMS | 18(28.6) | 13(50.0) | 1(2.4) | 5(13.5) | <.0001 |
| Headache | 12(19.1) | 10(38.5) | 13(31.7) | 13(35.1) | 0.1715 |
| NIHSS at enrollment | 6.75(6.5) | 11.04(8.4) | 1.46(2.5) | 2.06(2.5) | <.0001 |
| GCS (initial) | 13.9(2.2) | 12.54(3.2) | 15(0.0) | 14.81(0.6) | 0.0018 |
| TPA administered | 21(33.0) | — | 2(4.9) | 2(5.4) | <.0001 |
| ABCD2 score | — | — | 4.39(1.2) | — | |
| TOAST criteria | | | | | |
| 1(Atherosclerosis) | 21(33.3) | — | — | — | |
| 2(Cardioembolic) | 7(11.1) | — | — | — | |
| 3(small vessel occlusion) | 2(3.2) | — | — | — | |
| 4 (other determined cause) | 7(11.1) | — | — | — | |
| 5 (undetermined) | 26(41.3) | — | — | — | |
| Vascular distribution | | | | | |
| Anterior | 36(57.1) | — | — | — | |
| Lacunar | 7(11.1) | — | — | — | |
| Posterior | 9(14.3) | — | — | — | |
| >1 distribution | 2(3.2) | — | — | — | |

Discharge status, a proxy of functional status, varied greatly by diagnosis as is seen in Table 8. Among ischemic stroke and ICH patients, a smaller proportion were discharged home than among those with TIA and mimics (<0.0001). The length of stay varied significantly by diagnosis, as patients with ischemic strokes and ICH remained inpatient longer. ($p<0.0001$).

TABLE 8

Discharge destination as a proxy of functional status

| Characteristic | Ischemic Stroke N = 63 | ICH N = 26 | TIA N = 41 | Mimic N = 37 | Normal N = 70 | P-value |
|---|---|---|---|---|---|---|
| Length of stay | 6.47(5.6) | 10.4(6.5) | 2.4(2.9) | 1.81(2.1) | | <.0001 |
| Discharge status | | | | | | <.0001+ |
| Home | 34(53.97) | 9(34.62) | 37(90.25) | 36(97.29) | | |
| Rehabilitation | 11(17.46) | 6(23.08) | 2(4.88) | — | | |
| SNF | 8(12.7) | 7(26.92) | 2(4.88) | 1(2.7) | | |
| Hospice | 5(7.94) | 1(3.85) | — | | | |
| Deceased | 5(7.94) | 3(11.54) | — | | | |

However, when the coefficient were not fixed, these 3 variables predicted the log-odds of being an ischemic stroke patient versus healthy patient with a c-statististic of 0.842 (Hosmer-Lemeshow test p=0.8908).

To create one overall model to predict TIA and ICHs as well, each variable significant by multivariate regression in the TIA and ICH analyses was added to the 3-variable model and the new overall model was bootstrapped each time in the ischemic stroke vs. mimic analysis. Only variables which individually contributed to an overall increase of the c-index by 1% were retained. Of the 4 variables significant in the TIA analyses, only metalloproteinase inhibitor-4 (TIMP-4) met this criteria by increasing the c-index by 5% up to 0.9019. Of the 6 variables significant in the ICH analyses, only prolactin met the standard by increasing the overall concordance index of the now 4-variable model to 0.9183 (1.8% increase).

TABLE 9

Results of Multivariate Logistic Regressions

| Biomarker | AUC | P |
|---|---|---|
| Angiopoietin 2 | 0.681 | 0.0092 |
| EGFR | 0.619 | 0.0117 |
| Interleukin-1 receptor type II | 0.581 | 0.0364 |
| C-C motif chemokine 13 | 0.740 | 0.002 |
| Overall model c-statistic | 0.869 | |
| Ischemic Stroke vs. TIA + Mimic | | |
| Angiopoietin 2 | 0.680 | 0.0096 |
| Eotaxin | 0.728 | 0.0002 |
| Interleukin-1 receptor type II | 0.570 | 0.0139 |
| Metalloproteinase inhibitor-4 | 0.608 | 0.0061 |
| Overall model c-statistic | 0.845 | |
| Ischemic Stroke vs. Mimic | | |
| Eotaxin | 0.809 | 0.0005 |
| EGFR | 0.696 | 0.0153 |
| Protein S100 A12 | 0.607 | 0.0206 |
| Overall model c-statistic | 0.899 | |
| Ischemic Stroke + ICH vs. Mimic | | |
| Growth differentiation factor-15 | 0.489 | 0.0092 |
| Interleukin-1 receptor-like 1 | 0.718 | 0.0117 |
| Interleukin-8 | 0.750 | 0.0364 |
| Platelet endothelial cell adhesion molecule | 0.538 | 0.002 |
| Prolactin | 0.75 | 0.0074 |
| Overall model c-statistic | 0.900 | |
| Ischemic Stroke vs. ICH | | |
| Angiopoietin related protein 6 | 0.680 | .0096 |
| Interleukin-1 receptor-like 1 | 0.728 | .0002 |
| Overall model c-statistic | 0.954 | |

TABLE 10

Results of Multivariate Logistic Regressions comparing Ischemic Stroke + ICH vs. Mimic and Ischemic Stroke vs. ICH.

| Biomarker | AUC | P |
|---|---|---|
| Growth differentiation factor-15 | 0.489 | 0.0092 |
| Interleukin-1 receptor-like 1 | 0.718 | 0.0117 |
| Interleukin-8 | 0.750 | 0.0364 |
| Platelet endothelial cell adhesion molecule | 0.538 | 0.002 |
| Prolactin | 0.75 | 0.0074 |
| Overall model c-statistic | 0.900 | |

The final model consisted of 5 variables: eotaxin, EGFR, S100A12, TIMP-4, and prolactin. This model was internally validated with the bootstrapping technique in three comparison groups. (Table 11) When discriminating between ischemic strokes and mimics, the 5-variable model yielded a bootstrapped c-statistic of 0.9183 (95% CI: 0.909, 0.9276); a goodness of fit confirmed with a p of 0.1416 (Hosmer-Lemeshow test); an overall model likelihood ratio $\chi^2$ of 49.7161 (p<0.0001). When comparing the log-odds of ischemic stroke+ICH versus mimic, the 5-variable model bootstrapped c-statistic was 0.9273 (95% CI: 0.919, 0.9355); goodness of fit was confirmed with a Hosmer-Lemeshow test p of 0.5802; overall model likelihood ratio $\chi^2$ was 55.8567 (p<0.0001). Finally, when the 5 variables were used to regress the log-odds of ICH versus ischemic stroke, the bootstrapped c-statistic was 0.8958 (95% CI: 0.8806, 0.911); its goodness of fit confirmed by a Hosmer-Lemeshow test p-value of 0.9935; an overall model likelihood ratio $\chi^2$ of 13.5990 (p=0.0184).

TABLE 11

Results of Internal Validation by Bootstrapping

| Biomarker | Parameter estimate (95% CI) | P |
|---|---|---|
| Stroke v. Mimic | | |
| Eotaxin | .003 (−.00141, .005) | 0.0021 |
| EGFR v1 | .0018 (−.0013, .004) | 0.1914 |
| TIMP-4 | −.0004 (−.0008, .0005) | 0.3325 |
| Prolactin | .0001 (−.0001, .0002) | 0.2325 |
| S100A12 | −.1253 (−.2225, .1241) | 0.0621 |
| Intercept | −4.1563 (−7.2863, 1.2487) | 0.0503 |
| C-statistic | 0.9183(0.909, 0.9276) | |
| Stroke + ICH v. Mimic | | |
| Eotaxin | .0032(−.0013, .0145) | 0.0012 |
| EGFR v1 | .0019(−.0013, .004) | 0.1877 |
| TIMP-4 | −.0004(−.0008, .0004) | 0.3167 |
| Prolactin | .0001(−.0002, .0002) | 0.2158 |
| S100A12 | −.1278(−.2268, .1249) | 0.0607 |
| Intercept | −4.31(−7.334, 1.0617) | 0.0351 |
| C-statistic | 0.9273(0.919, 0.9355) | |
| Stroke v. ICH | | |
| Eotaxin | .00658(−.0083, .0145) | 0.26764 |
| EGFR v1 | −.00089(−.0148, .0176) | 0.45978 |
| TIMP-4 | −.00056(−.0018, .0018) | 0.31563 |
| Prolactin | .0007(−.0038, .0035) | 0.31035 |
| S100A12 | .0162(−.0918, .1074) | |
| Intercept | 1.8919(−21.7902, 18.3112) | |
| C-statistic | 0.8958(0.8806, 0.911) | |

Table 12 contains the sensitivities, specificities, PPV, and NPV from these models. The robustness of the 5-variable model was tested by the addition of TIA to the ischemic stroke group and then to the mimic group while keeping fixed the parameter estimates from the 5-variable model. When TIA patients were grouped with ischemic strokes, the c-statistic was 0.812, however, the model goodness of fit (p<0.0001) and likelihood ratio $\chi^2$ (0.711, p=0.9824) were poor. When TIA patients were grouped with mimic patients, the model fared better with a c-statistic of 0.824, model goodness of fit confirmed at p=0.4980, and likelihood ratio of 45.44 (p<0.0001).

The 5-variable model also predicted the log-odds of an anterior circulation versus a posterior circulation or lacunar stroke with fair accuracy (c=0.733). Goodness of fit was established with a Hosmer and Lemeshow probability of 0.2895. The only covariate with a Wald $\chi^2$ bordering statistical significance was prolactin (p=0.0807). Possible associations between each biomarker and age, race, and gender were tested with linear regressions. Prolactin was significantly associated with age (0.0362) with an adjusted R-squared of 0.0216; TIMP-4 with age (p<0.0001, adjusted R-squared=0.2525); and TIMP-4 with gender (p<0.0001, adjusted R-squared 0.0882). None of the 5 markers were significantly collinear (r>0.4) with each other.

TABLE 12

Discriminative capacity of the 5-biomarker model and the model with 5 biomarkers plus age, race and sex

| Probability | SENSITIVITY | SPECIFICITY | PPV | NPV |
|---|---|---|---|---|
| Ischemic Stroke vs. Mimic Predicted by Biomarkers | | | | |
| 0.10 | 90.6 | 50.0 | 51.8 | 90.0 |
| 0.30 | 81.3 | 77.8 | 68.4 | 87.5 |
| 0.38† | 78.1 | 79.6 | 69.4 | 86.0 |
| Ischemic Stroke vs. Mimic Predicted by Biomarkers, Age, Race, and Gender | | | | |
| 0.10 | 93.5 | 75.9 | 69.0 | 95.3 |
| 0.30 | 90.3 | 85.2 | 77.1 | 93.9 |
| 0.38† | 87.1 | 85.2 | 77.1 | 92 |
| Ischemic Stroke + ICH vs. Mimic Predicted by Biomarkers | | | | |
| 0.10 | 90.6 | 54.8 | 51.9 | 91.9 |
| 0.30 | 78.1 | 80.6 | 67.6 | 87.7 |
| 0.53† | 71.9 | 88.7 | 76.7 | 85.9 |
| Ischemic Stroke + ICH vs Mimic Predicted by Biomarkers, Age, Race, and Gender | | | | |
| 0.10 | 93.5 | 79.0 | 69 | 96.1 |
| 0.30 | 90.3 | 87.1 | 77.8 | 94.7 |
| 0.53† | 80.6 | 88.7 | 78.1 | 91.2 |

In this prospective, observational study, 5 biomarkers (eotaxin, epidermal growth factor receptor, S100A12, TIMP-4, and prolactin) robustly differentiated outcomes of interest including ischemic stroke, ICH, and stroke mimics. These are largely novel and not representative of the stroke biomarkers which dominate the literature such as markers of glial activation including S100B and GFAP and markers of neuronal injury such as NSE. The biomarkers in the final stroke model have pathophysiologic roles which lend biologic plausibility to their statistical association with stroke. Eotaxin is a potent chemokine for eosinophils and other inflammatory cells. Treatment of vascular endothelial cells with TNF-alpha resulted in a 20-fold induction of smooth muscles expression of eotaxin in human atheroma as well as an increase in macrophage and mast cell expression of CCR3, its receptor, suggesting eotaxin recruits inflammatory cells in atheromas. Another study demonstrated an increase in eotaxin in ischemic stroke patients versus healthy controls. Epidermal growth factor receptor (EGFR) and its ligands may play a role in regulation of genes associated with reactive gliosis. After an ischemic event, proliferating glial cells abundant in the infarcted brain and astrocytes in the periphery of the infarct were highly immunoreactive to EGFR.

As a chemoattractant for monocytic cells, S100A12 is an inflammatory response mediator. Its receptor, RAGE (receptor for advanced glycation end products), activates transcription factors that play an important role in protection from oxidative stress such as NF-κB. S100A12 was found to dramatically induce neurite outgrowth from rat embryonic hippocampal cells. Finally, plasma levels of S100A12 were higher in patients with carotid atherosclerosis and highest in patients with most recent symptoms.

TIMP-4 irreversibly inactivates metalloproteinases and is expressed in astrocytes, monocytes, platelets, smooth muscle cells, and endothelial cells. It is a major intraplatelet matrix metalloproteinase inhibitor, thus involved in regulating platelet recruitment and aggregation.

Prolactin is involved in platelet activation as P-selectin expression and platelet aggregation increase in its presence and in acute ischemic stroke patients. There is an isoform of the prolactin receptor on platelets, suggesting a mechanism similar to ADP-induced platelet aggregation. Moreover, patients with prolactinomas have an increased incidence of deep venous thromboembolism indicating that elevated prolactin may contribute to hypercoagulability.

One important feature of this biomarker test is its NPV. A clinically relevant question that an emergency medicine physician faces when presented with a patient with an acute neurologic deficit is whether the patient can be safely sent home. If the probability of stroke is set at its prevalence among patients who present to the emergency department with a neurologic problem, then the proportion of patients with a negative test who are correctly diagnosed by the biomarker test coupled with information about age, gender, and race is 94.7 percent when comparing ischemic stroke and ICH patients to mimics While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of treating ischemic stroke in a subject, comprising:

measuring C—C motif chemokine 13 in a body fluid sample obtained from the subject; correlating the result to the occurrence or nonoccurrence of ischemic stroke or likelihood of stroke in the subject, and administering tissue plasminogen activator (tPA) to the subject having a decrease in C—C motif chemokine 13 concentration in the body fluid sample compared to a threshold level.

2. The method according to claim 1, wherein said measuring step comprises introducing the body fluid sample obtained from the subject into an assay instrument which (i) contacts the body fluid sample with a binding reagent for C—C motif chemokine 13, wherein C—C motif chemokine 13 binds to its respective specific binding reagent in an amount related to its concentration in the body fluid sample, (ii) generates a result indicative of binding of C—C motif chemokine 13 to its respective specific binding reagent; and (iii) displays the result as a quantitative result in a human-readable form.

3. The method according to claim 1, wherein the sensitivity or specificity is at least 0.7 for the identification of ischemic stroke when compared to normal subjects.

4. The method according to claim 1, wherein the sensitivity or specificity is at least 0.7 for the identification of ischemic stroke when compared to subjects exhibiting symptoms that mimic stroke symptoms.

5. The method according to claim 1, wherein the sensitivity or specificity is at least 0.7 for the identification of ischemic stroke when compared to subjects exhibiting symptoms that mimic stroke symptoms and subjects suffering from TIA.

6. The method according to claim 1, wherein the body fluid sample is selected from the group consisting of blood, serum, and plasma.

* * * * *